United States Patent
Abdelmagid et al.

(10) Patent No.: US 9,421,253 B2
(45) Date of Patent: Aug. 23, 2016

(54) COMPOSITIONS FOR CANINE RESPIRATORY DISEASE COMPLEX

(75) Inventors: Omar Yousif Abdelmagid, Kalamazoo, MI (US); Joseph Michael Bricker, Kalamazoo, MI (US); Shelly Lynn Shields, Kalamazoo, MI (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 13/983,136

(22) PCT Filed: Feb. 3, 2012

(86) PCT No.: PCT/IB2012/050510
§ 371 (c)(1),
(2), (4) Date: Dec. 2, 2013

(87) PCT Pub. No.: WO2012/104820
PCT Pub. Date: Aug. 9, 2012

(65) Prior Publication Data
US 2014/0079733 A1    Mar. 20, 2014

Related U.S. Application Data

(60) Provisional application No. 61/439,597, filed on Feb. 4, 2011, provisional application No. 61/470,084, filed on Mar. 31, 2011.

(51) Int. Cl.
| | | |
|---|---|---|
| *A61K 39/145* | (2006.01) | |
| *A61K 39/215* | (2006.01) | |
| *A61K 39/10* | (2006.01) | |
| *A61K 39/295* | (2006.01) | |
| *A61K 39/02* | (2006.01) | |
| *A61K 39/12* | (2006.01) | |
| *A61K 39/00* | (2006.01) | |

(52) U.S. Cl.
CPC ........... *A61K 39/295* (2013.01); *A61K 39/099* (2013.01); *A61K 39/12* (2013.01); *A61K 39/145* (2013.01); *A61K 39/215* (2013.01); *A61K 2039/521* (2013.01); *A61K 2039/5252* (2013.01); *A61K 2039/5254* (2013.01); *A61K 2039/552* (2013.01); *A61K 2039/55505* (2013.01); *A61K 2039/55555* (2013.01); *A61K 2039/55566* (2013.01); *A61K 2039/55577* (2013.01); *A61K 2039/70* (2013.01); *C12N 2710/10334* (2013.01); *C12N 2760/16134* (2013.01); *C12N 2760/18734* (2013.01); *C12N 2770/20034* (2013.01)

(58) Field of Classification Search
None
See application file for complete search history.

(56) References Cited

U.S. PATENT DOCUMENTS

2004/0185602 A1 *  9/2004  Chaudhuri et al. ........... 438/108
2007/0082012 A1 *  4/2007  Shields et al. ............. 424/209.1

FOREIGN PATENT DOCUMENTS

| WO | WO 01-90143 | * 11/2001 |
|---|---|---|
| WO | WO 2004-011651 | * 2/2004 |
| WO | WO 2005-002618 | * 1/2005 |
| WO | WO 2006-038115 | * 4/2006 |
| WO | WO 2006-106424 | * 10/2006 |
| WO | WO 2007-118206 | * 10/2007 |

OTHER PUBLICATIONS

Medhekar et al (Molec. Microbio. 71(2): 492-504. Jan. 2009).*
Erles et al. "Detection of a group 2 coronavirus in dogs with canine infectious respiratory disease" Virology, 310 (2003) 216-223.
Crawford et al. "Transmission of Equine Influenza Virus to Dogs" Science, 310 (2005) 482-485.
Binn et al. "Viruses recovered from laboratory dogs with respiratory disease" Experimental Biology and Medicine, 126 (1967) 140-145.
Ditchfield et al. "Association of a canine adenovirus (Toronto A 26/61) with an outbreak of laryngotracheitis ("kennel cough")", Can Vet. Journal, 3 (1962) 238-247.
Chalker et al. "Mycoplasmas associated with canine infectious respiratory disease ", Microbiology, 150 (2004) 3491-3497.
Bemis et al. "Bacteriological variation among Bordetella bronchiseptica isolates from dogs and other species" Journal of Clinical Microbiology, 5(4) (1977) 471-480.
Anissa Cheung, Influenza Virus Vaccine 2015-2016 Strain Selection, Vaccines and Related Biological Products Advisory Committee (Mar. 4, 2015).
Jane Sykes, Canine Infectious Respiratory Disease: The Flu or Not the Flu?, pp. 1-5.
Canine respiratory coronavirus—Dog, http://www.vetbook.org/wiki/dog/index.php/Canine_respiratory_coronavirus, pp. 1-2.

* cited by examiner

*Primary Examiner* — Jennifer Graser
(74) *Attorney, Agent, or Firm* — Vyacheslav Vasilyev

(57) ABSTRACT

Provided herein are compositions comprising a canine influenza virus and a canine respiratory coronavirus. They can further comprise *Bordetella bronchiseptica*, pertactin, canine parainfluenza virus, and canine adenovirus serotype 2. The compositions are effective for treating or preventing canine respiratory diseases, including canine infectious respiratory disease complex.

13 Claims, 3 Drawing Sheets

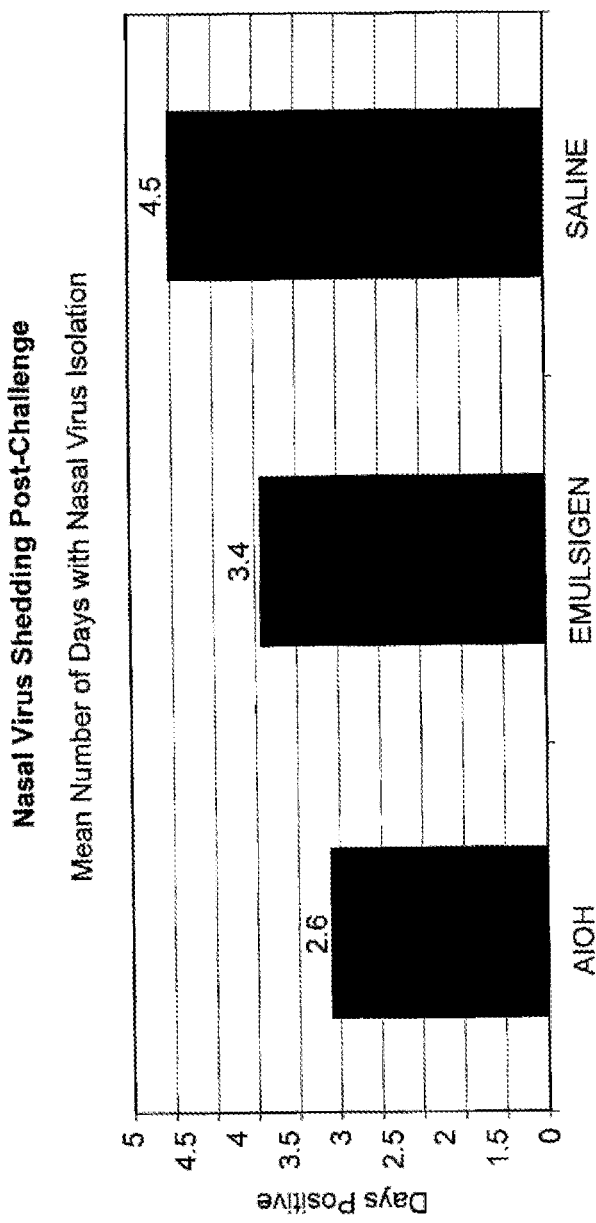

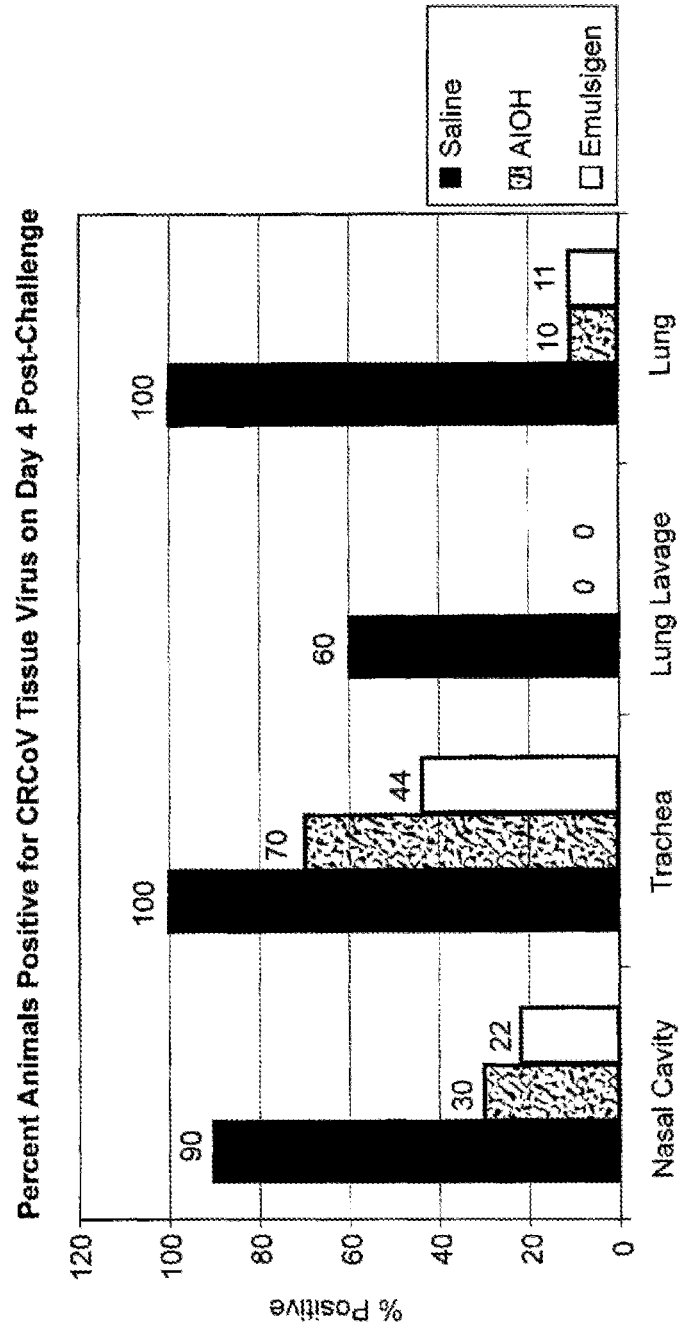

COMPOSITIONS FOR CANINE RESPIRATORY DISEASE COMPLEX

CROSS-REFERENCE TO RELATED APPLICATIONS

This application is a national phase entry of international application number PCT/IB2012/050510, filed Feb. 3, 2012, which claims priority to both U.S. Provisional Application No. 61/439,597, filed Feb. 4, 2011 and U.S. Provisional No. 61/470,084, filed Mar. 31, 2011. The disclosures of the above-identified provisional applications and the above-identified international application are herein incorporated by reference in their entireties.

FIELD OF THE INVENTION

The present invention relates to the field of immunology, and in particular to the field of immunogenic and vaccine compositions. It relates to such compositions for use against canine respiratory diseases, including canine infectious respiratory disease complex (CIRDC). The present invention also relates to methods for vaccinating against, treating, or preventing canine respiratory diseases in a canine.

BACKGROUND OF THE INVENTION

Canine infectious respiratory disease complex (CIRDC) is a highly contagious disease that is common in dogs housed in crowded conditions, such as re-homing centers and boarding or training kennels. Many dogs suffer only from a mild cough and recover after a short time. However in some cases, a severe bronchopneumonia can develop.

The pathogenesis of CIRDC is considered to be multi-factoral, involving several viruses and bacteria. Infectious agents known to be causative agents of CIRDC include canine respiratory coronavirus (CRCoV) (Erles et al., Virology, 310(2):216-223, 2003), canine influenza virus (CIV) (Crawford et al., Science, 310(5747):482-485, 2005), canine parainfluenzavirus (CPIV) (Binn et al., Exp. Biol. Med., 126:140-145, 1967), canine adenovirus serotype 2 (CAV-2) (Ditchfield et al., Can. Vet. J., 3:238-247, 1962), *Mycoplasma cynos* (Chalker et al., Microbiology, 150:3491-3497, 2004), and the bacterium *Bordetella bronchiseptica* (Bemis et al., Lab. Anim. Sci., 29:48-52, 1977).

CRCoV causes a highly contagious respiratory infection which is spread by direct dog-to-dog contact, aerosols of respiratory secretions, and contact with contaminated environments or people. Some dogs have a mild disease with symptoms consisting of cough, sneezing, and nasal discharge. Some dogs have a subclinical infection with no clinical signs, yet they shed virus that can infect other dogs. Some dogs infected with CRCoV progress to pneumonia, particularly if co-infected with other respiratory pathogens.

Regarding CIV, equine influenza virus has been recognized as a major respiratory pathogen in horses since about 1956. Disease symptoms caused by equine influenza virus can be severe, and are often followed by secondary bacterial infections. Two subtypes of equine influenza virus are recognized, namely subtype-1, the prototype being A/Equine/Prague/1/56 (H7N7), and subtype-2, the prototype being A/Equine/Miami/1/63 (H3N8). Presently, the predominant virus subtype is subtype-2, the H3N8 strain. An influenza virus, H3N8 equine influenza virus, is able to infect canines, with fatalities in some cases as high as 36%. One explanation is that an interspecies transfer of the complete or a portion of the equine influenza virus to the dog resulted in a new canine specific influenza virus associated with acute respiratory disease (Crawford et al., 2005).

Disease caused by CPIV is common in the upper respiratory tract. Disease caused by CPIV alone can be mild or subclinical, with signs becoming more severe if concurrent infection with other respiratory pathogens occurs.

CAV-2 causes respiratory disease which, in severe cases, can include pneumonia and bronchopneumonia.

*B. bronchiseptica* has been reported as being a primary etiological agent in the respiratory disease tracheobronchitis or "kennel cough". It predisposes dogs to the influence of other respiratory agents, and frequently exists concurrently with them. Kennel cough is typically a condition of the upper airways, and is characterized by nasal discharge and coughing. To date, a number of vaccines are available for treatment of tracheobronchitis caused by *Bordetella bronchiseptica*, including Nobivac®, Bronchi-Shield®, Bronchicine® CAe, Vanguard® B, Univac 2, Recombitek® KC2, Naramune™-2 and Kennel-Jec™2. However, the majority of existing commercial vaccines require cumbersome intranasal administration as well as the addition of adjuvants, which can result in deleterious side-effects, such as burning and irritation. Viera Scheibner et al., *Nexus* December 2000 (Vol 8, No 1). Subunit vaccines, such as those involving the use of p68 protein of *Bordetella bronchiseptica* (pertactin), have been explored but to date have not been included in any commercial canine vaccines, possibly due to insufficient immunogenicity, adverse reactions, and/or formulation stability.

The pathology of CIRDC indicates that it is involved in lung damage and, in some cases, bronchopneumonia, but it is distinct from kennel cough (primary etiological agent: *B. bronchiseptica*) which mainly involves upper respiratory tract changes. Kennel cough is a milder syndrome than CIRDC, and does not have the wide range of pathology noted in CIRDC. CIRDC is also distinguished by an increased severity and mortality.

CIRDC is rarely fatal, but it delays re-homing of dogs at rescue centers, disrupts schedules in training kennels, and results in considerable treatment costs and welfare concerns. Vaccines are available against some of the infectious agents associated with CIRDC. However, despite the use of these vaccines, CIRDC is still prevalent world-wide, possibly due to the lack of efficacious vaccines against all the infectious agents involved in CIRDC.

Accordingly, there remains a need for an immunogenic composition, capable of being safely administered to a canine, which provides long-acting immunoprotection against the agents that cause CIRDC without deleterious side effects or interference with other antigens in a combination vaccine. The present disclosure fulfils these and other related needs.

SUMMARY OF THE INVENTION

The present invention generally relates to immunogenic compositions which provide antigens that treat or prevent CIRDC. In one embodiment, an immunogenic composition comprises a canine influenza virus (CIV) and a canine respiratory coronavirus (CRCoV). In another embodiment, the immunogenic composition further comprises a *Bordetella bronchiseptica*. In another embodiment, the immunogenic composition further comprises an isolated pertactin antigen. In another embodiment, the immunogenic composition comprises a p68 pertactin antigen. In another embodiment, the pertactin antigen is a recombinant protein. In yet another embodiment, the pertactin antigen is present at between about 1 µg and about 30 µg. In another embodiment, said pertactin antigen is prepared by solubilizing pertactin inclusion bodies in urea and optionally purifying by column chromatography. Said pertactin antigens are soluble and preferably substantially free of aggregates. In another embodiment, the *Bordetella bronchiseptica* is a bacterin or a bacterial extract.

In one embodiment, the immunogenic composition comprises a CIV, a CRCoV, a *Bordetella bronchiseptica* and one or both antigens selected from canine parainfluenza virus (CPIV) and canine adenovirus type 2 (CAV-2). In another embodiment, said immunogenic composition further comprises a p68 pertactin antigen. In another embodiment, the *Bordetella bronchiseptica* is a bacterin or a bacterial extract.

Another embodiment provides an immunogenic composition comprising a CIV, CRCoV, a *Bordetella bronchiseptica* component comprising *Bordetella bronchiseptica* and an isolated pertactin antigen, and one or both antigens selected from canine parainfluenza virus (CPIV) and canine adenovirus type 2 (CAV-2). In a further embodiment, the immunogenic composition comprises both CPIV and CAV-2.

In another embodiment, the immunogenic composition of any one of the foregoing embodiments further comprises an isolated Bsp22 antigen.

In another embodiment, the immunogenic composition of any one of the foregoing embodiments is non-adjuvanted. In another embodiment, the immunogenic composition of any one of the foregoing embodiments comprises an adjuvant.

In another embodiment, the immunogenic composition of any one of the foregoing embodiments does not contain a non-respiratory antigen.

In yet another embodiment, the immunogenic composition of any one of the foregoing embodiments induces an immune response to a canine respiratory pathogen in a canine. In another embodiment, said canine respiratory pathogen is at least one of CIV, CRCoV, CPIV, CAV-2, *Bordetella bronchiseptica*, and *Mycoplasma cynos*.

Another embodiment of the present invention provides a use of the immunogenic composition of any one of the foregoing embodiments for the treatment or prevention of infection from a canine respiratory pathogen in a canine. In another embodiment, said canine respiratory pathogen is at least one of CIV, CRCoV, CPIV, CAV-2, *Bordetella bronchiseptica*, and *M. cynos*. In another embodiment, said composition prevents said infection for a period of about 6 months or more. In another embodiment, said composition prevents said infection for a period of about one year. In another embodiment, the present invention provides a use of the immunogenic composition of any one of the foregoing embodiments in the manufacture of a medicament for the treatment or prevention of infection from a canine respiratory pathogen in a canine.

Another embodiment of the present invention provides the immunogenic composition of any one of the foregoing embodiments wherein said composition treats or prevents canine infectious respiratory disease complex (CIRDC) in a canine. Another embodiment of the present invention provides a method of treating or preventing CIRDC in a canine comprising administering to said canine the immunogenic composition of any one of the foregoing embodiments. In another embodiment, said composition prevents CIRDC for a period of about 6 months or more. In another embodiment, said composition prevents CIRDC for a period of about one year. Another embodiment provides for a use of the immunogenic composition of any one of the foregoing embodiments in the manufacture of a medicament for the treatment or prevention of CIRDC in a canine.

BRIEF DESCRIPTION OF THE DRAWINGS

FIG. 2. Nasal Virus Shedding Post-Challenge. Measurement of CRCoV shed from the nasal passages when dogs were vaccinated with saline, AlOH-adjuvanted, or Emulsigen®-adjuvanted compositions, followed by subsequent challenge with CRCoV.

FIG. 3. Percent Animals Positive for CRCoV Tissue Virus on Day 4 Post-Challenge. Assessment of number of dogs positive for CRCoV in respiratory tissue when vaccinated with saline, AlOH-adjuvanted, or Emulsigen®-adjuvanted compositions, followed by subsequent challenge with CRCoV.

DETAILED DESCRIPTION OF THE INVENTION

Figure 1:
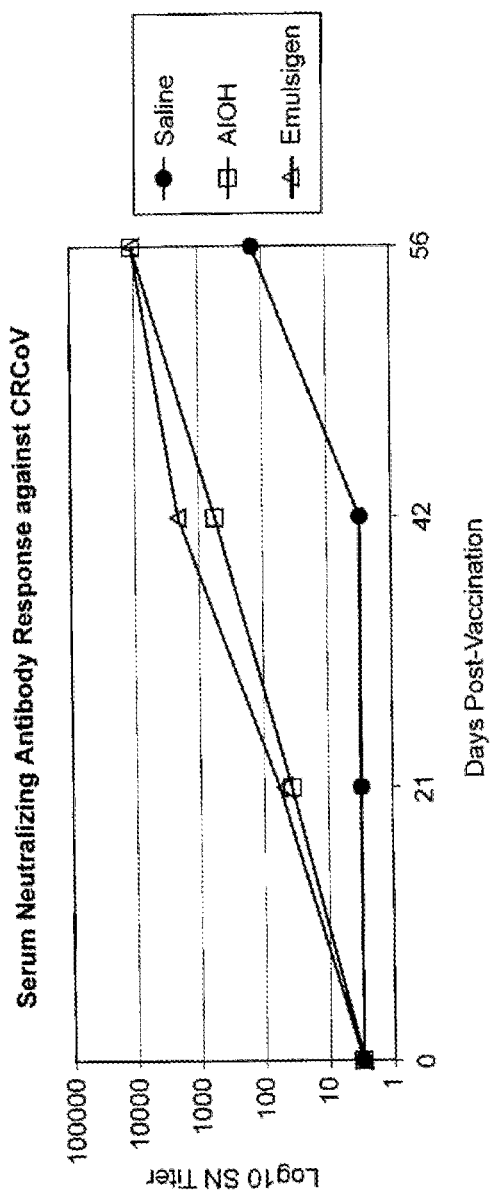
FIG. 1. Serum Neutralizing Antibody Response against CRCoV. Measurement of serum neutralizing antibody response against canine respiratory coronavirus (CRCoV) when dogs were vaccinated with saline, Aluminum hydroxide (AlOH)-adjuvanted, or Emulsigen®-adjuvanted compositions.

The definitions below apply to this disclosure. They supersede any contradictory definitions contained in each individual reference incorporated herein by reference. Words not defined have the meaning commonly used by one skilled in the art. Further, unless otherwise required by context, singular terms shall include pluralities and plural terms shall include the singular.

"About" or "approximately," when used in connection with a measurable numerical variable, refers to the indicated value of the variable and to all values of the variable that are within the experimental error of the indicated value (e.g., within the 95% confidence interval for the mean), or within 10 percent of the indicated value, whichever is greater. If "about" is used in reference to time intervals in weeks, "about 3 weeks" is 17 to 25 days, and "about 2 to about 4 weeks" is 10 to 40 days.

"Adjuvant", as used herein, refers to any substance which serves as a non-specific stimulator of the immune response. See below for a further description of adjuvants.

The term "animal", as used herein, includes any animal that is susceptible to canine respiratory disease complex, including mammals, both domesticated and wild.

"Antibody", as used herein, is any polypeptide comprising an antigen-binding site regardless of the source, method of production, or other characteristics. It refers to an immunoglobulin molecule or a fragment thereof that specifically binds to an antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions. An antibody that is "specific" for a given antigen indicates that the variable regions of the antibody recognize and bind a specific antigen exclusively. The term includes, but is not limited to: a polyclonal antibody, a monoclonal antibody, a monospecific antibody, polyspecific antibody, humanized antibody, a tetrameric antibody, a tetravalent antibody, a multispecific antibody, a single chain antibody, a domain-specific antibody, a single domain antibody, a domain-deleted antibody, a fusion protein, an ScFc fusion protein, a single-chain antibody, chimeric antibody, synthetic antibody, recombinant antibody, hybrid antibody, mutated antibody, and CDR-grafted antibodies. Antibodies can be intact immunoglobulins derived from natural sources or from recombinant sources, or can be immunoreactive portions of intact immunoglobulins. An "antibody" can be converted to an antigen-binding protein, which includes but is not limited to antibody fragments which include but are not limited to: Fab, F(ab')$_2$, an Fab' fragment, an Fv fragment, a single-chain Fv (ScFv) fragment, an Fd fragment, a dAb fragment, diabodies, a CDR3 peptide, a constrained FR3-CDR3-FR4 peptide, a nanobody, a bivalent nanobody, a small modular immunopharmaceutical (SMIPs), and a minibody and any of above mentioned fragments and their chemically or genetically manipulated counterparts, as well as other antibody fragments that retain antigen-binding function. Typically, such fragments would comprise an antigen-binding domain. As will be recognized by those of skill in the art, any of such molecules may be engineered (for example "germlined") to decrease its immunogenicity, increase its affinity, alter its specificity, or for other purposes.

"Antigen" or "immunogen", as used herein, refers to a molecule that contains one or more epitopes (linear, conformational or both) that upon exposure to a subject will induce an immune response that is specific for that antigen. An epitope is the specific site of the antigen which binds to a T-cell receptor or specific antibody, and typically comprises about 3 amino acid residues to about 20 amino acid residues. The term antigen refers to subunit antigens—antigens separate and discrete from a whole organism with which the antigen is associated in nature—as well as killed, attenuated or inactivated bacteria, viruses, fungi, parasites or other microbes. The term antigen also refers to antibodies, such as anti-idiotype antibodies or fragments thereof, and to synthetic peptide mimotopes that can mimic an antigen or antigenic determinant (epitope). The term antigen also refers to an oligonucleotide or polynucleotide that expresses an antigen or antigenic determinant in vivo, such as in DNA immunization applications.

"Antigenicity", as used herein, refers to the capability of a protein or polypeptide to be immunospecifically bound by an antibody raised against the protein or polypeptide.

The term "*Bordetella bronchiseptica*" or "*B. bronchiseptica*" refers to: a live attenuated bacterium of *Bordetella bronchiseptica*, a killed whole cell extract (bacterin) of *Bordetella bronchiseptica* or a cellular bacterial extract of *Bordetella bronchiseptica*.

"Buffer" means a chemical system that prevents change in the concentration of another chemical substance. Proton donor and acceptor systems serve as buffers, preventing marked changes in hydrogen ion concentration (pH). A further example of a buffer is a solution containing a mixture of a weak acid and its salt (conjugate base), or a weak base and its salt (conjugate acid).

"Canine", as used herein, includes what is commonly called the dog, but includes other members of the family Canidae.

The term "cell line" or "host cell", as used herein, means a prokaryotic or eukaryotic cell in which a virus can replicate or be maintained.

The term "culture", as used herein, means a population of cells or microorganisms growing in the absence of other species or types.

"Dose" refers to a vaccine or immunogenic composition given to a subject. A "first dose" or "priming dose" refers to the dose of such a composition given on Day 0. A "second dose" or a "third dose" or an "annual dose" refers to an amount of such composition given subsequent to the first dose, which can be but is not required to be the same vaccine or immunogenic composition as the first dose.

An "epitope" is the specific site of the antigen which binds to a T-cell receptor or specific antibody, and typically comprises from about 3 amino acid residues to about 20 amino acid residues.

"Excipient", as used herein, refers to a non-reactive carrier component of a vaccine or immunogenic composition that is not an antigen.

"Fragment" refers to a truncated portion of a protein or gene. "Functional fragment" and "biologically active fragment" refer to a fragment that retains the biological properties of the full length protein or gene.

"Homology" or "percent homology" refers to the percentage of nucleotide or amino acid residues in the candidate sequence that are identical or similar with the residues in the comparator sequence(s) after aligning the sequences and introducing gaps, if necessary, to achieve the maximum percent sequence homology, and also considering any conservative substitutions as part of the sequence homology.

"Homologs" or "species homologs" include genes found in two or more different species which possess substantial polynucleotide sequence homology, and possess the same, or similar, biological functions and/or properties. Preferably polynucleotide sequences which represent species homologs will hybridize under moderately stringent conditions, as described herein by example, and possess the same or similar biological activities and/or properties. In another aspect, polynucleotides representing species homologs will share greater than about 60% sequence homology, greater than about 70% sequence homology, greater than about 80% sequence homology, greater than about 90% sequence homology, greater than about 95% sequence homology, greater than about 96% sequence homology, greater than about 97% sequence homology, greater than about 98% sequence homology, or greater than about 99% sequence homology.

"Identity" or "percent identity" refers to the percentage of nucleotides or amino acids in the candidate sequence that are identical with the residues in the comparator sequence after aligning both sequences and introducing gaps, if necessary, to achieve the maximum percent sequence identity, and not considering any conservative substitutions as part of the sequence identity.

"Immune response", as used herein, in a subject refers to the development of a humoral immune response, a cellular immune response, or a humoral and a cellular immune response to an antigen. A "humoral immune response" refers to one that is at least in part mediated by antibodies. A "cellular immune response" is one mediated by T-lymphocytes or other white blood cells or both, and includes the production of cytokines, chemokines and similar molecules produced by activated T-cells, white blood cells, or both. Immune responses can be determined using standard immunoassays and neutralization assays, which are known in the art.

"Immunogenicity", as used herein, refers to the capability of a protein or polypeptide to elicit an immune response directed specifically against an antigen.

An "immunogenic composition" is a preparation containing an immunogen, including, e.g., a protein, a peptide, a whole cell, inactivated, subunit or attenuated virus, or a polysaccharide, or combination thereof, administered to stimulate the recipient's humoral and cellular immune systems to one or more of the antigens present in the immunogenic composition. "Immunization" is the process of administering an immunogenic composition and stimulating an immune or immunogenic response to an antigen in a host. Preferred hosts are mammals, such as dogs. Preferably, the immunogenic composition is a vaccine.

"Immunologically protective amount", as used herein, is an amount of an antigen effective to induce an immunogenic response in the recipient that is adequate to prevent or ameliorate signs or symptoms of disease, including adverse health effects or complications thereof. Either humoral immunity or cell-mediated immunity or both can be induced. The immunogenic response of an animal to a composition can be evaluated, e.g., indirectly through measurement of antibody titers, lymphocyte proliferation assays, or directly through monitoring signs and symptoms after challenge with wild type strain. The protective immunity conferred by a composition or vaccine can be evaluated by measuring, e.g., reduction of shed of challenge organisms, reduction in clinical signs such as mortality, morbidity, temperature, and overall physical condition, health and performance of the subject. The immune response can comprise, without limitation, induction of cellular and/or humoral immunity. The amount of a composition or vaccine that is therapeutically effective can vary, depending on the particular organism used, or the condition of the animal being treated or vaccinated, and can be determined by a veterinarian.

"Intranasal" administration, as used herein, refers to the introduction of a substance, such as a vaccine or other composition, into a subject's body through or by way of the nose, and involves transport of the substance primarily through the nasal mucosa.

"Isolated", as used herein, means removed from its naturally occurring environment, either alone or in a heterologous host cell, or chromosome or vector (e.g., plasmid, phage, etc.). "Isolated bacteria," "isolated anaerobic bacteria," "isolated bacterial strain," "isolated virus" "isolated viral strain" and the like refer to a composition in which the bacteria or virus are substantial free of other microorganisms, e.g., in a culture, such as when separated from it naturally occurring environment. "Isolated," when used to describe any particularly defined substance, such as a polynucleotide or a polypeptide, refers to the substance that is separate from the original cellular environment in which the substance—such as a polypeptide or nucleic acid—is normally found. As used herein therefore, by way of example only, a recombinant cell line constructed with a polynucleotide of the invention makes use of the "isolated" nucleic acid. Alternatively, if a particular protein or a specific immunogenic fragment is claimed or used as a vaccine or other composition, it would be considered to be isolated because it had been identified, separated and to some extent purified as compared to how it may exist in nature. If the protein or a specific immunogenic fragment thereof is produced in a recombinant bacterium or eukaryote expression vector that produces the antigen, it is considered to exist as an isolated protein or nucleic acid. For example, a recombinant cell line constructed with a polynucleotide makes use of an "isolated" nucleic acid.

"Medicinal agent" refers to any agent which is useful in the prevention, cure, or improvement of a medical condition, or the prevention of some physiological condition or occurrence.

"Monoclonal antibody", as used herein, refers to antibodies produced by a single line of hybridoma cells, all directed towards one epitope on a particular antigen. The antigen used to make the monoclonal antibody can be provided as an isolated protein of the pathogen or the whole pathogen. A "hybridoma" is a clonal cell line that consists of hybrid cells formed by the fusion of a myeloma cell and a specific antibody-producing cell. In general, monoclonal antibodies are of mouse origin. However, monoclonal antibody also refers to a clonal population of an antibody made against a particular epitope of an antigen produced by phage display technology, or method that is equivalent to phage display, or hybrid cells of non-mouse origin.

"Oral" or "peroral" administration, as used herein, refers to the introduction of a substance, such as a vaccine or other composition, into a subject's body through or by way of the mouth and involves swallowing or transport through the oral mucosa (e.g., sublingual or buccal absorption) or both. Intratracheal is also a means of oral or peroral administration.

"Oronasal" administration, as used herein, refers to the introduction of a substance, such as a composition or vaccine, into a subject's body through or by way of the nose and the mouth, as would occur, for example, by placing one or more droplets in the nose. Oronasal administration involves transport processes associated with oral and intranasal administration.

"Parenteral administration", as used herein, refers to the introduction of a substance, such as a composition or vaccine, into a subject's body through or by way of a route that does not include the digestive tract. Parenteral administration includes subcutaneous, intramuscular, intraarterial, and intravenous administration. For the purposes of this disclosure, parenteral administration excludes administration routes that primarily involve transport of the substance through mucosal tissue in the mouth, nose, trachea, and lungs.

The term "pathogen" or "pathogenic microorganism", as used herein, means a microorganism—for example, CPIV, CAV-2, CRCoV, CIV, or *Bordetella bronchiseptica*—which is capable of inducing or causing a disease, illness, or abnormal state in its host animal.

"Pertactin", as used herein, refers to an outer membrane protein of *Bordetella*. Preferably the pertactin is from *B. bronchiseptica* and most preferably, "p68", and is encoded by the gene, prnA. Pertactin can be isolated in its native form from *Bordetella bronchiseptica*, or it can be produced recombinantly. Sequences and examples of pertactin are provided in U.S. Pat. No. 7,736,658, the content of which is hereby incorporated by reference. The pertactin antigen used herein includes lipidated forms of the protein.

"Pharmaceutically acceptable" refers to substances which, within the scope of sound medical judgment, are suitable for use in contact with the tissues of subjects without undue toxicity, irritation, allergic response, and the like, commensurate with a reasonable benefit-to-risk ratio, and effective for their intended use.

"Polyclonal antibody", as used herein, refers to a mixed population of antibodies made against a particular pathogen or antigen. In general, the population contains a variety of antibody groups, each group directed towards a particular epitope of the pathogen or antigen. To make polyclonal antibodies, the whole pathogen, or an isolated antigen, is introduced by inoculation or infection into a host, which induces the host to make antibodies against the pathogen or antigen.

The term "polynucleotide", as used herein, means an organic polymer molecule composed of nucleotide monomers covalently bonded in a chain. DNA (deoxyribonucleic acid) and RNA (ribonucleic acid) are examples of polynucleotides with distinct biological function.

The term "polypeptide", as used herein, means an organic polymer molecule composed of two or more amino acids bonded in a chain.

"Preventing infection", as used herein, means to prevent or inhibit the replication of the bacteria or virus which causes the identified disease, to inhibit transmission of the bacteria or virus, to prevent the bacteria or virus from establishing itself in its host, or to alleviate the symptoms of the disease caused by infection. The treatment is considered therapeutic if there is a reduction in bacterial or viral load.

"Protection", "protecting", "protective immunity", and the like, as used herein with respect to a vaccine or other composition, means that the vaccine or composition prevents or reduces the symptoms of the disease caused by the organism from which the antigen(s) used in the vaccine or composition is derived. The terms "protection", "protecting", and the like, also mean that the vaccine or composition can be used to "treat" the disease, or one or more symptoms of the disease that already exists in a subject.

"Respiratory" administration, as used herein, refers to the introduction of a substance, such as a vaccine or other composition, into a subject's body through or by way of inhalation of a nebulized (atomized) substance. In respiratory administration, the primary transport mechanism involves absorption of the atomized substance through the mucosa in the trachea, bronchi, and lungs and is therefore different than intranasal or peroral administration.

The terms "specific binding," "specifically binds," and the like, are defined as two or more molecules that form a complex that is measurable under physiologic or assay conditions and is selective. An antibody or other inhibitor is said to "specifically bind" to a protein if, under appropriately selected conditions, such binding is not substantially inhibited, while at the same time non-specific binding is inhibited. Specific binding is characterized by high affinity and is selective for the compound or protein. Nonspecific binding usually has low affinity. Binding in IgG antibodies, for example, is generally characterized by an affinity of at least about $10^{-7}$ M or higher, such as at least about $10^{-8}$ M or higher, or at least about $10^{-9}$ M or higher, or at least about $10^{-10}$ or higher, or at least about $10^{-11}$ M or higher, or at least about $10^{-12}$ M or higher. The term is also applicable where, e.g., an antigen-binding domain is specific for a particular epitope that is not carried by numerous antigens, in which case the antibody carrying the antigen-binding domain will generally not bind other antigens.

"Specific immunogenic fragment", as used herein, refers to a portion of a sequence that is recognizable by an antibody or T cell specific for that sequence.

"Subject", as used herein, refers to any animal having an immune system, which includes mammals, such as dogs.

"Substantially identical", as used herein, refers to a degree of sequence identity of at least about 90%, at least about 95%, at least about 96%, at least about 97%, at least about 98%, or at least about 99%.

"Subunit vaccine", and "subunit composition", as used herein, refers to a type of vaccine or composition that includes one or more antigens—but not necessarily all antigens in the vaccine or composition—which are derived from or homologous to, antigens from a pathogen of interest, such as a virus, bacterium, parasite or fungus. Such a composition or vaccine is substantially free of intact pathogen cells or pathogenic particles, or the lysate of such cells or particles. Thus, a subunit vaccine or subunit composition can be prepared from at least partially purified, or substantially purified, immunogenic polypeptides from the pathogen or their analogs. Methods of obtaining an antigen or antigens in the subunit vaccine or subunit composition include standard purification techniques, recombinant production, or chemical synthesis. A "subunit vaccine" or "subunit composition" thus refers to a vaccine or composition consisting of a defined antigenic component or components of a virus, bacterium, or other immunogen.

"$TCID_{50}$" refers to "tissue culture infective dose" and is defined as that dilution of a virus required to infect 50% of a given batch of inoculated cell cultures. Various methods can be used to calculate $TCID_{50}$, including the Spearman-Karber method, which is utilized throughout this specification. For a description of the Spearman-Karber method, see B. W. Mahy & H. O. Kangro, *Virology Methods Manual* 25-46 (1996).

"Therapeutic agent", as used herein, refers to any molecule, compound, virus or treatment, preferably a virus attenuated or killed, or subunit or compound, that assists in the treatment of a viral, bacterial, parasitic or fungal infection, disease or condition caused thereby.

"Therapeutically effective amount", as used herein, refers to an amount of an antigen or vaccine or composition that would induce an immune response in a subject (e.g., dog) receiving the antigen or vaccine or composition which is adequate to prevent or ameliorate signs or symptoms of disease, including adverse health effects or complications thereof, caused by infection with a pathogen, such as a virus, bacterium, parasite or fungus. Humoral immunity or cell-mediated immunity, or both humoral and cell-mediated immunity, can be induced. The immunogenic response of an animal to an antigen, vaccine, or composition can be evaluated indirectly through measurement of antibody titers, lymphocyte proliferation assays, or directly through monitoring signs and symptoms after challenge with the wild type strain. The protective immunity conferred by a vaccine or composition can be evaluated by measuring reduction of challenge organism shed, and/or reduction in clinical signs, such as mortality, morbidity, temperature, and overall physical condition, health, and performance of the subject. The amount of a vaccine or composition that is therapeutically effective can vary, depending on the particular immunogen used, or the condition of the subject, and can be determined by one skilled in the art.

"Treat" or "treating", as used herein, refers to reversing, alleviating, inhibiting the progress of, or preventing a disorder, condition or disease to which such term applies, or to preventing one or more symptoms of such disorder, condition or disease.

"Treatment", as used herein, refers to the act of "treating", as defined immediately above.

"Vaccine" or "vaccine composition," as used herein, refers to an immunogenic composition selected from a virus or bacteria, either modified live, attenuated, or killed, or a subunit vaccine, or any combination of the aforementioned. Administration of the vaccine to a subject results in an immune response. The vaccine can be introduced directly into the subject by any known route of administration, including parenterally, perorally, and the like. The terms mean a composition which prevents or reduces an infection, or which prevents or reduces one or more signs or symptoms of infection. The protective effects of a vaccine composition against a pathogen are normally achieved by inducing in the subject an immune response. Generally speaking, abolished or reduced incidences of infection, amelioration of the signs or symptoms, or accelerated elimination of the microorganism from the infected subjects are indicative of the protective effects of a vaccine composition. The vaccine compositions of the present invention provide protective effects against infections caused by canine respiratory disease pathogens.

"Veterinarily acceptable", as used herein, refers to substances which are, within the scope of sound medical judgment, suitable for use in contact with the tissues of veterinary subjects without undue toxicity, irritation, allergic response, and the like, commensurate with a reasonable benefit-to-risk ratio, and effective for their intended use.

"Veterinarily acceptable carrier", as used herein, refers to a carrier medium that does not interfere with the effectiveness of the biological activity of the active ingredient, and is not toxic to the veterinary subject to whom it is administered.

Antigens, Immunogenic Compositions, and Vaccines

The present disclosure provides immunogenic compositions and vaccines comprising one or more viruses and bacteria. The present disclosure provides immunogenic compositions and vaccines comprising one or more viruses and bacteria or subunits that are suitable for administration to a canine for treatment against CIRDC.

The canine respiratory coronavirus (CRCoV) described herein can be characterised as a coronavirus present in the respiratory tracts of dogs with infectious respiratory disease. CRCoV is phylogenetically most closely related to bovine coronavirus (BCoV), human coronavirus (HCoV) strain OC43 and hemagglutinating encephalomyelitis virus (HEV); enteric canine coronavirus (CCoV) is only distantly related to CRCoV. A representative example of a CRCoV suitable for use in the present invention includes a strain identified as CRCoV strain 4182 (Erles et al., Virus Res., 124:78-87, 2007).

The influenza virus antigens encompassed by this invention can be any identified influenza virus strain, from any bird or mammal, including but not limited to, influenza virus having the subtype H3 hemagglutinin and subtype N8 neuraminidase, or the H3N8 subtype, more commonly referred to as an H3N8 virus. The influenza can be of mammalian or avian origin, including but not limited to swine, equine or canine origin. In one embodiment a canine influenza antigen is used. In one embodiment an equine influenza antigen is used. In one embodiment, a strain having the subtype glycoproteins designated H3 or N8 is used. In one embodiment, a strain having both subtype H3 and N8 glycoproteins is used.

The influenza antigens encompassed by this invention can be isolated from dogs, horses, pigs, and fowl, both domestic and wild. The animals chosen for sample collection should display acute and/or sub-acute clinical syndromes, which can include mild to severe respiratory symptoms and fever. Animals can also exhibit signs of anorexia and lethargy. Methods of virus isolation are well known to those skilled in the art including: inoculating mammalian or avian cell cultures, inoculating embryonated eggs with nasal or pharyngeal mucus samples from clinical specimens, collection by swabbing of the nasal passage or throat, or by collecting tissues such as spleen, lung, tonsil and liver and lung lavage. The cytopathic effect of the virus can be observed in cell culture. Allantoic fluid or cell lysates can be tested for their ability to agglutinate human, chicken, turkey or guinea pig red blood cells, presumptive evidence for the presence of an influenza virus.

A representative example of an influenza strain suitable for use in the present invention includes a strain identified as A/canine/Iowa/9A1/B5/08/D12, which was deposited as PTA-7694 on 29 Jun. 2006 at the American Type Culture Collection (ATCC), 10801 University Boulevard, Manassas, Va. 20110-2209, in compliance with Budapest Treaty on the International Recognition of the Deposit of Microorganisms for the Purposes of Patent Procedure. A representative strain of the CIV antigen is the CIV virus strain in the commercial vaccine, Vanguard® CIV (Pfizer, Inc). This invention also encompasses vaccines comprising a strain identified as Equine Influenza Strain A/Equine/2/Miami/1/63. This strain was deposited at the ATCC, with accession number VR 317, in compliance with Budapest Treaty on the International Recognition of the Deposit of Microorganisms for the Purposes of Patent Procedure.

Additional examples of influenza viruses for use in the present invention are A/canine/Iowa/13628/2005, A/Equine/Kentucky/1998, A/Equine/Kentucky/15/2002, A/Equine/Ohio/1/2003, A/Equine/Kentucky/1/1994, A/Equine/Massachusetts/213/2003, A/Equine/Wisconsin/2003, A/Equine/NewYork/1999, and A/Equine/Newmarket/A2/1993. Other preferred strains and/or isolates of CIV include those disclosed in U.S. Pat. No. 7,959,929 (particularly strains and HA sequences identified therein as Jacksonville/2005, Miami/2005, FL/242/03 and Florida/43/04), U.S. Pat. Nos. 7,384,642, 7,572,620 and 7,468,187, the contents of which, including all sequences, particularly HA sequences, and strains, are hereby incorporated by reference as if set forth fully herein. Additionally, a CIV strain suitable for use herein includes the Colorado CIV isolate described in Barrell et al., J. Vet. Intern. Med., 24 (6), 1524-1527 (2010), having accession number ADW41784.

The canine parainfluenza virus (CPIV) encompassed by this invention can be characterized as one of the viruses known to be a causative agent associated with kennel cough. A representative strain of the CPIV antigen is the attenuated CPI virus strain in the commercial vaccine, Vanguard® Plus 5 (Pfizer). Another representative strain of the CPIV antigen is the attenuated CPI virus strain having the designation of "NL-CPI-5" (National Veterinary Service Laboratory, Ames, Iowa).

The canine adenovirus, type 2 (CAV-2) encompassed by this invention can be characterized as one of the viruses also known to be a causative agent associated with kennel cough. A representative strain of the CAV-2 antigen is the attenuated CAV-2 virus strain in the commercial vaccine, Vanguard® Plus 5 (Pfizer). A representative strain of the CAV-2 antigen is the attenuated CAV-2 strain designated as the "Manhattan" strain (National Veterinary Service Laboratory, Ames, Iowa).

The *Mycoplasma cynos* (*M. cynos*) encompassed by this invention is described in Chalker et al., Microbiology, 150:3491-3497, 2004 and is the only species of mycoplasma commonly associated with respiratory disease. Immunogenic compositions against *M. cynos* are described in US 2007/0098739, incorporated herein by reference.

The *Bordetella bronchiseptica* component encompassed by this invention can be characterized as the bacterial causative agent associated with kennel cough. The immunogenic compositions and vaccines encompassed by the present invention can be one or more of: a live attenuated *Bordetella bronchiseptica*, a *Bordetella bronchiseptica* bacterin or a bacterial extract. Additionally, the composition preferably also includes an isolated subunit antigen of *Bordetella bronchiseptica*.

In one embodiment the *Bordetella bronchiseptica* is prepared as a whole cell sonicate purified through column chromatography as provided in Patent Application No. FR2571618, filed Oct. 12, 1984. Another representative example of a *Bordetella bronchiseptica* is the bacterial extract Bronchicine™ CAe (Pfizer), which is prepared from antigenic material extracted from *Bordetella bronchiseptica* cells. Another example of *Bordetella bronchiseptica* is the live attenuated *Bordetella bronchiseptica* strain B-C2 present in Nobivac® and/or the live bronchiseptica strain from Intra-Trac®, Bronchi-Shield®, Naramune™, Recombitek®, Univac, and/or Kennel-Jec™.

Additionally, a subunit is preferably also present (i.e., supplemented), in combination with the *Bordetella bronchiseptica* component. A representative example of the subunit is an isolated pertactin antigen, preferably, a *Bordetella bronchiseptica* p68 antigen, particularly the recombinant *Bordetella bronchiseptica* p68 antigen which is recognized by the p68-specific monoclonal antibody Bord 2-7 (described in U.S. Pat. No. 7,736,658, which is incorporated herein by reference) and in one preferred embodiment, has an amino acid sequence as set forth in U.S. Pat. No. 7,736,658 or having homology thereto.

The recombinant p68 pertactin antigen is preferably prepared in a soluble form, such that native-like structure is preserved or restored during processing. Accordingly, one aspect of the invention provides a recombinant p68 that is substantially free (less than about 80%, 90%, 95% or even 99%) of aggregates. In another embodiment the recombinant p68 is solubilised with urea, preferably about 0.1 M, 0.5 M, 1 M, 2 M, 3 M, or 6 M solution of urea. Thereafter, the p68 antigen can be purified, such as through column chromatography. One such solubilisation process is described in Surinder et al., J. Bioscience and Bioengineering, v. 99(4), pgs 303-310 (2005).

Pertactin antigens used herein also include lipidated forms. Examples of production of lipidated proteins is provided in Erdile et al., Infection and Immunity, (1993) v. 61(1), p. 81-90, incorporate by reference. The methods disclosed therein can be used to prepare posttranslationally modified pertactin proteins that contain an attached lipid moiety.

Furthermore, in another embodiment, an immunogenic composition comprises *Bordetella bronchiseptica* and an isolated Bsp22 antigen. In another embodiment, the immunogenic composition comprises *Bordetella bronchiseptica*, an isolated pertactin antigen, and an isolated Bsp22 antigen. The Bsp22 antigen can be prepared as provided in Medhekar et al., Molecular Microbiology (2009) 71(2), 492-504. Preferably, the isolated Bsp22 antigen is present in conjunction with (i.e., in addition to) a *Bordetella bronchiseptica* extract and an isolated pertactin antigen, specifically recombinant p68.

"Bsp22" also includes lipidated forms of the antigen. Examples of production of lipidated proteins is provided in Erdile et al., Infection and Immunity, (1993) v. 61(1), p. 81-90, incorporated by reference. The methods disclosed therein can be used to prepare posttranslationally modified Bsp22 proteins that contain an attached lipid moiety.

Viruses encompassed by the present invention can be propagated in cells, cell lines and host cells. Said cells, cell lines or host cells can be for example, but not limited to, mammalian cells and non-mammalian cells, including insect and plant cells. Cells, cell lines, and host cells in which viruses encompassed by the present invention can be propagated are readily known, and accessible to those of ordinary skill in the art.

In another embodiment, the immunogenic compositions described herein do not comprise non-respiratory antigens. Thus, one embodiment of the invention provides a composition as described herein with the proviso that it does not include a non-respiratory antigen. The non-respiratory antigens do not cause respiratory disease in a subject. Non-limiting examples of such non-respiratory antigens include rabies virus, canine parvovirus, enteric canine coronavirus, *Leptospira* species, and *Borrelia burgdorferi*.

Bacteria encompassed by the present invention can be cultured and propagated using various culture media known to those of ordinary skill in the art, including both broth (liquid) and agar (solid; semi-solid) cultivation media. Some bacteria can also be cultured and propagated in mammalian cells or non-mammalian cells.

The viruses and bacteria encompassed by the present invention can be attenuated or inactivated prior to use in an immunogenic composition or vaccine. Methods of attenuation and inactivation are well known to those skilled in the art. Methods for attenuation include, but are not limited to, serial passage in cell culture on a suitable cell line (viruses and some bacteria), serial passage in broth culture (bacteria), ultraviolet irradiation (viruses and bacteria), and chemical mutagenesis (viruses and bacteria). Methods for viral or bacterial inactivation include, but are not limited to, treatment with formalin, betapropriolactone (BPL) or binary ethyleneimine (BEI), or other methods known to those skilled in the art.

Inactivation by formalin can be performed by mixing the suspension containing the microorganism with 37% formaldehyde to a final formaldehyde concentration of 0.5%. The microorganism-formaldehyde mixture is mixed by constant stirring for approximately 24 hours at room temperature. The inactivated microorganism mixture is then tested for residual live organisms by assaying for growth on a suitable cell line or broth media.

For some antigens, inactivation by BEI can be performed by mixing the suspension containing the microorganism of the present invention with 0.1 M BEI (2-bromo-ethylamine in 0.175 N NaOH) to a final BEI concentration of 1 mM. For other antigens, the final BEI concentration is 2 mM. One skilled in the art would know the appropriate concentration to use. The virus-BEI mixture is mixed by constant stirring for approximately 48 hours at room temperature, followed by the addition of 1.0 M sodium thiosulfate to a final concentration of 0.1 mM. Mixing is continued for an additional two hours. The mixture containing the inactivated microorganism is tested for residual live virus by assaying for growth on a suitable cell line or broth media.

Immunogenic compositions and vaccines encompassed by the present invention can include one or more veterinarily-acceptable carriers. As used herein, a "veterinarily-acceptable carrier" includes any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others known to those skilled in the art. Stabilizers include albumin, among others known to the skilled artisan. Preservatives include merthiolate, among others known to the skilled artisan.

The adjuvant can be metabolizable, referring to adjuvants consisting of components that are capable of being metabolized by the target species such as vegetable oil based adjuvants. A metabolizable adjuvant can be a metabolizable oil. Metabolizable oils are fats and oils that typically occur in plants and animals, and usually consist largely of mixtures of triacylglycerols, also known as triglycerides or neutral fats. These nonpolar, water insoluble substances are fatty acid triesters of glycerol. Triacylglycerols differ according to the identity and placement of their three fatty acid residues or side chains.

The adjuvant can also be non-metabolizable, referring to adjuvants consisting of components that cannot be metabolized by the body of the animal subject to which the emulsion is administered. Non-metabolizable oils suitable for use in compositions of the present invention include alkanes, alkenes, alkynes, and their corresponding acids and alcohols, the ethers and esters thereof, and mixtures thereof. Preferably, the individual compounds of the oil are light hydrocarbon compounds, i.e., such components have 6 to 30 carbon atoms. The oil can be synthetically prepared or purified from petroleum products. Preferred non-metabolizable oils for use in compositions described herein include mineral oil, paraffin oil, and cycloparaffins, for example. The term "mineral oil" refers to a non-metabolizable adjuvant oil that is a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. Mineral oil can be obtained from various commercial sources, for example, J. T. Baker (Phillipsburg, Pa.), USB Corporation (Cleveland, Ohio). Light mineral oil is commercially available under the name DRAKEOL®.

Adjuvants include, but are not limited to, the Emulsigen® adjuvant system (MVP Laboratories; Ralston, Nebr.), the RIBI adjuvant system (Ribi Inc.; Hamilton, Mont.), alum, aluminum hydroxide gel, oil-in water emulsions, water-in-oil emulsions such as, e.g., Freund's complete and incomplete adjuvants, Block copolymer (CytRx; Atlanta, Ga.), SAF-M (Chiron; Emeryville, Calif.), AMPHIGEN® adjuvant, saponin, Quil A, QS-21 (Cambridge Biotech Inc.; Cambridge, Mass.), GPI-0100 (Galenica Pharmaceuticals, Inc.; Birmingham, Ala.) or other saponin fractions, monophosphoryl lipid A, Avridine lipid-amine adjuvant, heat-labile enterotoxin from *E. coli* (recombinant or otherwise), cholera toxin, muramyl dipeptide, squalene/pluronic block copolymer/surfactant (SP-oil), sulpholipobeta-cyclodextrin (SL-CD), liposomes containing an immunomodulator (e.g., CpG or poly I:C), muramyl dipeptide (MDP), iscomatrix (Quil A/phosphotidyl choline), CpG/DEAE-dextran/mineral oil (TXO), CpG, triterpenoids (e.g., Quil A or another purified or partially purified saponin preparation), sterols (e.g., cholesterol), immunomodulatory agents (e.g., dimethyl dioctadecyl ammonium bromide—DDA), polymers (e.g., polyacrylic acid such as CARBOPOL®), and Th2 stimulants (e.g., glycolipids such as Bay R1005®), and combinations thereof, among many other adjuvants known to those skilled in the art.

Non-limiting examples of various combinations that can be used include a triterpenoid plus a sterol (e.g., Quil A/cholesterol, also known as QAC), a triterpenoid plus a sterol, an immunomodulatory agent, and a polymer (e.g., Quil A/cholesterol/DDA/CARBOPOL®, also known as QCDC), and a triterpenoid plus a sterol, an immunomodulatory agent, a polymer, and a Th2 stimulant (e.g., Quil A/cholesterol/DDA/CARBOPOL®, and Bay R1005®, also known as QCDCR).

The amounts and concentrations of adjuvants and additives useful in the context of the present invention can readily be determined by the skilled artisan. In one embodiment, the present invention contemplates immunogenic compositions and vaccines comprising from about 20 µg to about 2000 µg of adjuvant. In another embodiment, adjuvant is included in an amount from about 100 µg to about 1500 µg, or from about 250 µg to about 1000 µg, or from about 350 µg to about 750 µg. In another embodiment, adjuvant is included in an amount of about 500 µg/2 ml dose of the immunogenic composition or vaccine.

The immunogenic compositions and vaccines can also include antibiotics. Such antibiotics include, but are not limited to, those from the classes of aminoglycosides, carbapenems, cephalosporins, glycopeptides, macrolides, penicillins, polypeptides, quinolones, sulfonamides, and tetracyclines. In one embodiment, the present invention contemplates immunogenic compositions and vaccines comprising from about 1 µg/ml to about 60 µg/ml of antibiotic. In another embodiment, the immunogenic compositions and vaccines comprise from about 5 µg/ml to about 55 µg/ml of antibiotic, or from about 10 µg/ml to about 50 µg/ml of antibiotic, or from about 15 µg/ml to about 45 µg/ml of antibiotic, or from about 20 µg/ml to about 40 µg/ml of antibiotic, or from about 25 µg/ml to about 35 µg/ml of antibiotic. In yet another embodiment, the immunogenic compositions and vaccines comprise less than about 30 µg/ml of antibiotic.

Immunogenic compositions and vaccines encompassed by the present invention can include one or more polynucleotide molecules encoding for a virus or bacteria, or viral or bacterial protein. DNA or RNA molecules can be used in immunogenic compositions or vaccines. The DNA or RNA molecule can be administered absent other agents, or it can be administered together with an agent facilitating cellular uptake (e.g., liposomes or cationic lipids). Total polynucleotide in the immunogenic composition or vaccine will generally be between about 0.1 µg/ml and about 5.0 mg/ml. In another embodiment, the total polynucleotide in the immunogenic composition or vaccine can be from about 1 µg/ml and about 4.0 mg/ml, or from about 10 µg/ml and about 3.0 mg/ml, or from about 100 µg/ml and about 2.0 mg/ml. Vaccines and vaccination procedures that utilize nucleic acids (DNA or mRNA) have been well described in the art, for example, U.S. Pat. No. 5,703,055, U.S. Pat. No. 5,580,859, and U.S. Pat. No. 5,589,466, all of which are incorporated herein by reference.

In addition to the viruses or bacteria described above, immunogenic compositions and vaccines encompassed by the present invention can include other additional antigens. Antigens can be in the form of an inactivated whole or partial preparation of the microorganism, or in the form of antigenic molecules obtained by genetic engineering techniques or chemical synthesis. Other antigens appropriate for use in accordance with the present invention include, but are not limited to, those derived from pathogenic viruses such as canine distemper virus, canine herpesvirus, canine influenza virus, rabies virus, pathogenic bacteria such as *Bordetella bronchiseptica, Leptospira bratislava, Leptospira canicola, Leptospira grippotyphosa, Leptospira icterohaemorrhagiae, Leptospira pomona, Leptospira hardjobovis, Porphyromonas* spp., *Bacteriodes* spp., *Borrelia* spp., *Streptococcus* spp., including *Streptococcus equi* subspecies *zooepidemicus, Ehrlichia* spp., *Mycoplasma* spp., including *Mycoplasma cynos*, and *Microsporum canis*. Antigens can also be derived from pathogenic fungi such as *Candida*, protozoa such as *Cryptosporidium parvum, Neospora caninum, Toxoplasma gondii, Eimeria* spp., *Babesia* spp., *Giardia* spp., *Leishmania* spp., or helminths such as *Taenia, Cuterebra, Echinococcus*, and *Paragonimus* spp.

Forms, Dosages, Routes of Administration

Immunogenic compositions and vaccines encompassed by the present invention can be administered to animals to induce an effective immune response against CIRDC. Accordingly, the present invention provides methods of stimulating an effective immune response by administering to an animal a therapeutically effective amount of an immunogenic composition or vaccine described herein.

Immunogenic compositions and vaccines described herein can be administered to an animal to vaccinate the animal subject against CIRDC. The immunogenic compositions and vaccines can be administered to the animal to prevent or treat CIRDC in the animal. Accordingly, described herein are methods of vaccinating an animal against CIRDC, and preventing or treating CIRDC, comprising administering to the animal a therapeutically effective amount of an immunogenic composition or vaccine described herein.

Immunogenic compositions and vaccines encompassed by the present invention can be made in various forms depending upon the route of administration. For example, the immunogenic compositions and vaccines can be made in the form of sterile aqueous solutions or dispersions suitable for injectable use, or made in lyophilized forms using freeze-drying techniques. Lyophilized immunogenic compositions and vaccines are typically maintained at about 4° C., and can be reconstituted in a stabilizing solution, e.g., saline or HEPES, with or without adjuvant. Immunogenic compositions and vaccines can also be made in the form of suspensions or emulsions.

Immunogenic compositions and vaccines of the present invention include a therapeutically effective amount of one or more of the above-described microorganisms. Purified viruses and/or bacteria can be used directly in an immunogenic composition or vaccine, or can be further attenuated, or inactivated. Typically, an immunogenic composition or vaccine contains between about $1 \times 10^2$ and about $1 \times 10^{12}$ viral or bacterial particles, or between about $1 \times 10^3$ and about $1 \times 10^{11}$ particles, or between about $1 \times 10^4$ and about $1 \times 10^{10}$ particles, or between about $1 \times 10^5$ and about $1 \times 10^9$ particles, or between about $1 \times 10^6$ and about $1 \times 10^5$ particles. The precise amount of a microorganism in an immunogenic composition or vaccine effective to provide a protective effect can be determined by a skilled artisan.

The pertactin antigen is present at between about 1 µg and about 30 µg. More particularly, said pertactin is present at between about 5 µg and about 20 µg, more particular still, at between about 7 µg and about 15 µg, and even more particularly, at about 5 µg, 10 µg, 15 µg or 20 µg.

The immunogenic compositions and vaccines generally comprise a veterinarily-acceptable carrier, in a volume of between about 0.5 ml and about 5 ml. In another embodiment the volume of the carrier is between about 1 ml and about 4 ml, or between about 2 ml and about 3 ml. In another embodiment, the volume of the carrier is about 1 ml, or is about 2 ml, or is about 5 ml. Veterinarily-acceptable carriers suitable for use in immunogenic compositions and vaccines can be any of those described hereinabove.

Those skilled in the art can readily determine whether a virus or bacteria needs to be attenuated or inactivated before administration. In another embodiment of the present invention, a virus or bacterium can be administered directly to an animal without additional attenuation. The amount of a microorganism that is therapeutically effective can vary, depending on the particular microorganism used, the condition of the animal and/or the degree of infection, and can be determined by a skilled artisan.

In accordance with the methods of the present invention, a single dose can be administered to animals, or, alternatively, two or more inoculations can take place with intervals of from about two to about ten weeks. Boosting regimens can be required, and the dosage regimen can be adjusted to provide optimal immunization. Those skilled in the art can readily determine the optimal administration regimen.

Immunogenic compositions and vaccines can be administered directly into the bloodstream, into muscle, into an internal organ, or under the skin. Suitable means for parenteral administration include intravenous, intraarterial, intramuscular, and subcutaneous administration. Suitable devices for parenteral administration include needle (including microneedle) injectors and needle-free injectors.

Parenteral formulations are typically aqueous solutions which can contain excipients such as salts, carbohydrates, proteins, and buffering agents (preferably to a pH of from about 3 to about 9, or from about 4 to about 8, or from about 5 to about 7.5, or from about 6 to about 7.5, or about 7 to about 7.5), but, for some applications, they can be more suitably formulated as a sterile non-aqueous solution or as a dried form to be used in conjunction with a suitable vehicle such as sterile, pyrogen-free water or saline.

The preparation of parenteral formulations under sterile conditions, for example, by lyophilization, can readily be accomplished using standard pharmaceutical techniques well known to those skilled in the art.

The solubility of materials used in the preparation of parenteral solutions can be increased by the use of appropriate formulation techniques known to the skilled artisan, such as the incorporation of solubility-enhancing agents, including buffers, salts, surfactants, liposomes, cyclodextrins, and the like.

Compositions for parenteral administration can be formulated to be immediate or modified release. Modified release formulations include delayed, sustained, pulsed, controlled, targeted and programmed release. Thus, immunogenic compositions and vaccines can be formulated as a solid, semi-solid, or thixotropic liquid for administration as an implanted depot, providing modified release of the immunogenic compositions and vaccines.

Other means of immunogenic composition or vaccine administration include delivery by microneedle or needle-free (e.g. Powderject™, Bioject™, etc.) injection.

In cases where subcutaneous or intramuscular injection is used, an isotonic formulation is preferred. Generally, additives for isotonicity can include sodium chloride, dextrose, mannitol, sorbitol, and lactose. In particular cases, isotonic solutions such as phosphate buffered saline are used. The formulations can further encompass stabilizers such as gelatin and albumin. In some embodiments, a vaso-constrictive agent is added to the formulation. The pharmaceutical preparations according to the present invention are generally provided sterile and pyrogen-free. However, it is well known by those skilled in the art that the formulations for the pharmaceutically accepted carrier are those pharmaceutical carriers approved in the regulations promulgated by the United States Department of Agriculture, or equivalent government agency in a foreign country such as Canada or Mexico, or any one of the European nations, for any canine vaccine, polypeptide (antigen) subunit immunogenic compositions and vaccines, recombinant virus vector vaccines, and DNA vaccines. Therefore, the pharmaceutically accepted carrier for commercial production of the immunogenic compositions or vaccines is a carrier that is already approved or will be approved by the appropriate government agency in the United States of America or foreign country. The immunogenic compositions and vaccines can further be mixed with an adjuvant that is pharmaceutically acceptable. In certain formulations of the immunogenic compositions and vaccines, the immunogenic composition or vaccine is combined with other canine immunogenic compositions or vaccines to produce a polyvalent product that can protect canine against a wide variety of diseases caused by other canine pathogens.

The immunogenic compositions described herein can prevent infection from a canine respiratory pathogen or can prevent CIRDC in a canine for a period of about three months or more. The compositions can prevent infection from said canine respiratory pathogen or can prevent CIRDC in said canine for a period of about six months or more. The compositions can prevent infection from said canine respiratory pathogen or can prevent CIRDC in said canine for a period of about one year.

Detection and Diagnostic Methods

The extent and nature of the immune responses induced in the animal can be assessed by using a variety of techniques. For example, sera can be collected from the inoculated animals, and tested for the presence or absence of antibodies specific for the immunogens. Detection of responding cytotoxic T-lymphocytes (CTLs) in lymphoid tissues, indicative of the induction of a cellular immune response, can be achieved by assays such as T cell proliferation. The relevant techniques are well described in the art.

Kits

Inasmuch as it may be desirable to administer an immunogenic composition or vaccine in combination with additional compositions or compounds—for example, for the purpose of treating a particular disease or condition—it is within the scope of the present invention that an immunogenic composition or vaccine can conveniently be included in, or combined in, the form of a kit suitable for administration or co-administration of the compositions.

Thus, kits encompassed by the present invention can comprise one or more separate pharmaceutical compositions, at least one of which is an immunogenic composition or vaccine in accordance with the present invention, and a means for separately retaining said compositions, such as a container, divided bottle, or divided foil packet. An example of such a kit is a syringe and needle, and the like. A kit of the present invention is particularly suitable for administering different dosage forms, for example, oral or parenteral, for administering the separate compositions at different dosage intervals, or for titrating the separate compositions against one another. To assist one administering a composition encompassed by the present invention, the kit typically comprises directions for administration.

Another kit encompassed by the present invention can comprise one or more reagents useful for the detection of an infected animal. The kit can include reagents for analyzing a sample for the presence of whole microorganisms, polypeptides, epitopes or polynucleotide sequences. The presence of virus, bacteria, polypeptides, or polynucleotide sequences can be determined using antibodies, PCR, hybridization, and other detection methods known to those of skill in the art.

Another kit encompassed by the present invention can provide reagents for the detection of antibodies against particular epitopes. Such reagents are useful for analyzing a sample for the presence of antibodies, and are readily known and available to one of ordinary skill in the art. The presence of antibodies can be determined using standard detection methods known to those of skill in the art.

In certain embodiments, the kits can include a set of printed instructions, or a label indicating that the kit is useful for the detection of infected animals.

Antibodies

Antibodies can either be monoclonal, polyclonal, or recombinant. The antibodies can be prepared against the immunogen or a portion thereof. For example, a synthetic peptide based on the amino acid sequence of the immunogen, or prepared recombinantly by cloning techniques, or the natural gene product and/or portions thereof can be isolated and used as the immunogen. Immunogens can be used to produce antibodies by standard antibody production technology well known to those skilled in the art. Antibody fragments can also be prepared from the antibodies by methods known to those skilled in the art, and include Fab, $F(ab')_2$, and Fv fragments.

In the production of antibodies, screening for the desired antibody can be accomplished by standard methods in immunology known in the art. In general, ELISAs and Western blotting are the preferred types of immunoassays. Both assays are well known to those skilled in the art. Both polyclonal and monoclonal antibodies can be used in the assays. The antibody can be bound to a solid support substrate, conjugated with a detectable moiety, or be both bound and conjugated as is well known in the art. The binding of antibodies to a solid support substrate is also well known in the art. The detectable moieties contemplated for use in the present invention can include, but are not limited to, fluorescent, metallic, enzymatic and radioactive markers such as biotin, gold, ferritin, alkaline phosphatase, b-galactosidase, peroxidase, urease, fluorescein, rhodamine, tritium, $^{14}C$, and iodination.

The present invention is further illustrated by, but by no means limited to, the following examples.

EXAMPLES

Example 1

Evaluation of CRCoV-Containing Vaccines

Sixty 8 to 9-week-old beagle dogs in good general health were used in the study. All animals received physical examination upon arrival and again on study day −2 or −1. Animals were observed once daily for general health status from arrival study day −8 to study day 39. Tympanic temperatures were collected starting on study day −1 prior to vaccination. Blood samples (approximately 5 mL) for serology were collected in SST tubes on study days 0 and 21 prior to each vaccination.

The CRCoV vaccine strain was derived from strain CRCoV.669, deposited as PTA-11444 on 28 Oct. 2010 at the American Type Culture Collection (ATCC), 10801 University Boulevard, Manassas, Va. 20110-2209, in compliance with Budapest Treaty on the International Recognition of the Deposit of Microorganisms for the Purposes of Patent Procedure. The CIV vaccine strain was derived from that deposited with the ATCC as PTA-7694. The CPIV and CAV-2 isolates were derived from virus seeds used to formulate vaccines in the Vanguard® vaccine line (Pfizer). The antigens were prepared at the highest passages of virus (Master Seed Virus+5). The vaccine compositions contained an adjuvant consisting of Quil A (20 ug), cholesterol (20 ug), dimethyl dioctadecyl ammonium bromide (DDA; 10 ug), and Carbopol® (a polyacrylic acid; 0.05% v/v). The CRCoV antigen was formulated to target 1.3 relative antigen units (RAU) per dose. Experimental vaccines were tested for sterility.

A heterologous CRCoV isolate ("Max" strain; passage 1) was used as the challenge material. The virus stock material was propagated and titered on HRT18G cells, and was determined to have a titer of $10^{7.1}$ TCID$_{50}$/mL. This challenge material was tested and confirmed satisfactory for sterility, and free of mycoplasma or canine/feline extraneous agents.

One animal was vaccinated on day 21; all remaining animals were vaccinated on study day 22. Animals were vaccinated subcutaneously with the appropriate vaccine or placebo according to the study design shown in Table 1. The first vaccination was administered in the right shoulder region (study day 0) and the second vaccination was administered in the left shoulder region (study day 22).

lobes were evaluated grossly for lung lesions (consolidation). Each lung lobe was scored for percentage of lung consolidation. One lung set had insufficient exsanguination, and was not evaluated. The trachea was transected, the lumen evaluated for gross pathology, and any findings were recorded.

After the lungs had been scored, the right caudal lung lobe was lavaged by flushing with approximately 30.0 mL of media for bacteriological analysis and virus isolation. A pair of tissue samples was collected from the trachea and the

TABLE 1

Study Design

| Group | IVP | N | Vaccination[1] Study Days | Route | Challenge[2] Study Day | Dose | Necropsy Study Day |
|---|---|---|---|---|---|---|---|
| T01 | Adjuvanted Placebo QuilA/cholesterol/DDA/Carbopol (QC/DC) | 10 | 0 and 22 | SC | 42 | $10^6$ $TCID_{50}$ | 46 |
| T02 | Adjuvanted Placebo (QC/DC) | 10 | | | | | 56 |
| T03 | CRCoV/CIV/CPIV/CAV2 (QC/DC) | 10 | | | | | 46 |
| T04 | CRCoV/CIV/CPIV/CAV2 (QC/DC) | 10 | | | | | 56 |
| T05 | CRCoV monovalent RTU (QC/DC; emulsified) | 10 | | | | | 46 |
| T06 | CRCoV monovalent RTU (QC/DC; emulsified) | 10 | | | | | 56 |

[1]Investigational Veterinary Product (IVP) was administered (SC) subcutaneously.
[2]Challenge dose with CRCoV Max isolate at passage 1 intranasally.
RTU: Ready-to-use liquid vaccine.

After the first vaccination, animals were observed daily (from study days 1 through 8) for post vaccination injection swelling. After the second vaccination, animals were observed daily for post vaccination injection swelling through day 29. Observations were continued twice weekly for animals that had injection site swelling/pain beyond the days listed above, until swelling/pain resolved. Tympanic temperatures were collected daily for one week after each vaccination.

Blood samples (approximately 8 mL) for serology were collected in SST tubes on study day 42 prior to challenge. Tympanic temperatures were collected on study days 40, 41, and 42 pre-challenge. Two types of oropharyngeal swabs (VTM [Virus Transport Medium] for virus isolation, and Amies for bacterial isolation) were collected from each dog prior to challenge on study day 42. Animals were observed once daily pre-challenge on study days 40, 41, and 42, for clinical signs of respiratory disease to establish baseline values.

On study day 42, all animals were challenged intranasally (IN) with the CRCoV challenge virus at a target challenge dose of $10^6$/mL/dog. All animals were sedated prior to challenge administration by intravenous injection of Domitor®. After sedation, each animal received 1.0 mL of challenge virus, given approximately 0.5 mL per nostril slowly using a syringe without a needle. After challenge administration, sedation was reversed by an intramuscular injection of Antisedan®. Tympanic temperatures, clinical observations, and oropharyngeal swabs were collected daily post-challenge from study day 42 to 56. Blood samples (approximately 5 mL) for serology were collected on study day 46 and study day 56 (prior to necropsy).

At necropsy, the complete lung and trachea was aseptically removed and placed on a sterile drape, and the lung nasal cavity, one for virus isolation and the second for histopathology. The right cranial lung lobes were divided into three samples, including one for bacteriology sampling. Blood for serology was collected on pre-determined study days.

Results.

All animals were confirmed by IFA testing to be negative for antibodies (IFA titer <40) against CRCoV before study day 0. Oropharyngeal swabs evaluated for CRCoV virus isolation confirmed that all animals were free of CRCoV on study day 0 prior to vaccination. Placebo-vaccinated controls remained CRCoV seronegative until study day 42. The group was confirmed CRCoV-free by virus isolation on study day 42, indicating lack of extraneous CRCoV in the facility. All dogs were confirmed to be free of *Bordetella bronchiseptica* on study day 42.

An ELISA assay was used to measure the CRCoV antigen concentration in the vaccine as relative antigen unit (RAU) against a specific batch of CRCoV designated reference antigen. CRCoV antigen was determined to be 0.5 RAU/dose.

Following vaccination, the majority of the vaccinated dogs, including the placebo-vaccinated group, developed an injection swelling at the injection site. For the monovalent vaccinated group, the swelling sizes were generally small (2 cm or less in the longest dimension) in the majority of the vaccinates. These swellings resolved within two weeks for the majority of the dogs. There was no pain or systemic reactions related to the vaccine in any of the vaccinated dogs. No clinical fever (≥39.5° C.) was observed, except in one dog, although the elevated temperature in that dog was not related to vaccination (the temperature was collected prior to the second vaccination). These findings indicate that the monovalent vaccine causes only injection swellings within what is expected for an adjuvanted vaccine.

Serum neutralization titers were tabulated and compared between groups. All monovalent-vaccinated dogs (100%) developed SN titers (GMT 371) three weeks after the second vaccination, indicating active immunization. A strong post-challenge (anamnestic) serum-neutralizing response was measured on day 56 in the combination vaccinated dogs (GMT 6,915) compared to the placebo-vaccinated dogs (GMT 471). These results were statistically significantly different, and indicate that the CRCoV vaccine antigen effectively stimulated and primed the immune responses of dogs against CRCoV infection.

Following challenge, all placebo-vaccinated animals (100%) shed virus in their oropharyngeal secretions at least for one day between day 1 and day 6 post-challenge, indicating induction of CRCoV infection. The monovalent vaccine significantly reduced (p=0.0237) the mean number of days with oropharyngeal shedding (2.1 days) when compared to placebo (3.3 days), indicating vaccine efficacy in reducing CRCoV infection.

All placebo-vaccinated dogs (100%) tested positive for virus isolation on day 4 post-challenge in their trachea, nasal cavity, and lungs, indicating CRCoV infection of the respiratory organs. There was no virus isolated from any organ on day 14 post-challenge, suggesting a typical respiratory viral infection similar to canine influenza. By contrast, the monovalent vaccine prevented infection in 90% and 50% of the vaccinated dogs' lungs (p-value <0.0001) and trachea (p-value <0.0237), respectively. This indicates that the monovalent vaccine induced sufficient immunity that prevented virus infection in these critical organs. There were no significant differences in the rate of nasal cavity infection between vaccinates and controls.

The CRCoV challenge caused only mild clinical signs under experimental conditions. Ocular and nasal discharges and conjunctivitis were reported in dogs across treatment groups. There were 5 animals reported with clinical fever (≥39.5° C.) during the post challenge period—two in the placebo groups, one in a monovalent vaccine group, and two in the combination vaccine groups.

Gross evaluation of the lungs, trachea, and nasal turbinates was performed on day 4 and 14 post-challenge. There was no remarkable gross lesion reported, except that two dogs—one in T05, one in T01—had low levels of lung consolidation; Two dogs—one in T01, one in T03 had focal areas of necrosis in the nasal turbinates.

For histopathology, lung, trachea, and nasal cavity tissues were examined and scored. Depending on the extent of changes observed, a score (0 to 4) was assigned. Changes attributable to the challenge were most notable in the nasal turbinates, then the trachea, and finally the lungs. This is consistent with a respiratory challenge virus that has its primary effect on the upper respiratory tract (nasal turbinates and trachea), with a subsequent and lesser effect on the lower respiratory tract (lung). This demonstrates that the CRCoV infection caused tissue pathology in the respiratory organs.

Previous studies have shown that ciliary damage in the trachea on day 4 post-challenge is a characteristic pathologic sequel of CRCoV infection. The data showed that the monovalent vaccine prevented tracheal ciliary damage in 60% of the animals when compared to placebo vaccinated (30% normal animals), but the reduction was not significant (P=0.1538). Diagnostic bacteriology performed on lungs and lung lavages confirmed that all animals were negative for *Bordetella bronchiseptica*, *Pasteurella* spp., *Staphlyococcus intermedius* and *Streptococcus canis*. Lung, lung lavage, or both were positive for *Mycoplasma* spp. in only 4 animals. This finding suggests that the lesions were specific for, and resulting from, the virus infection.

In summary, all CRCoV-vaccinated dogs (100%) in 103-106 developed serum neutralizing titers three weeks after the second vaccination, indicating active immunization. The monovalent vaccine induced immune responses in the vaccinates that reduced virus shedding in oropharyngeal secretions and in respiratory organs. It also reduced tracheal ciliary damage in vaccinates compared to placebo-vaccinated controls. The histopathological examination showed that the monovalent vaccine prevented tracheal ciliary damage in 60% of the animals when compared to placebo-vaccinated animals (30%).

Example 2

Efficacy Testing of a Bivalent CRCoV/CIV Vaccine in Dogs

Sixty 7- to 8-week old beagle dogs in good general health were used in the study. All animals received a physical examination upon arrival on study day −9. All animals, with the exception of one dog that was removed on study day −7, received a second physical examination on study day −2, and deemed suitable for the study. Animals were observed once daily for general health status from arrival study day −7 to study day 39. Blood samples (approximately 6 mL) for serology were collected in serum separation tubes (SST) on study days 0 and 21 prior to each vaccination. Two sets of nasal swabs—one for CRCoV and one for CIV virus isolation—were collected from each dog prior to vaccination on Day 0 to confirm freedom from CRCoV and CIV. Tympanic temperature was collected and documented on Days −1 and 0 prior to vaccination, to establish a baseline prior to vaccination. Tympanic temperatures were collected prior to second vaccination on Day 21. Animals were palpated on the shoulder region on study days 0 and 21 prior to vaccination, to ensure that no pre-existing lesions were present on the injection site area.

One dog in T04 was removed from the study due to respiratory distress on study day −7. One dog in T05 was removed from the study due to respiratory distress on study day 0 prior to vaccination. Additionally, two animals were removed from the study post-inclusion due to conditions unrelated to the conduct of the study. One dog in T06 was removed from study on study day 21 prior to receiving the second vaccination due to respiratory distress. One dog in T02 was removed from the study on day 21 prior to receiving the second vaccination, due to unresolved kerato-conjunctivitus and prolapsed nictitans.

Two bivalent vaccines were prepared, an inactivated CRCoV/inactivated CIV vaccine adjuvanted with Emulsigen® at 5% v/v, and an inactivated CRCoV/inactivated CIV vaccine adjuvanted with Rehydragel™ at 5% v/v (Table 2). The CRCoV vaccine strain was derived from that deposited with the ATCC as PTA-11444. The CIV vaccine strain was derived from what was deposited with the ATCC as PTA-7694. Both antigen bulks used to make the vaccines were produced at maximum passage of virus and cells, to meet immunogenicity requirements. The CRCoV antigen was formulated to target 1.55 RAU/dose. The CIV antigen was formulated to target 640 HA Units/dose.

TABLE 3

Study Design

| Group | IVP | N | Vaccination[1] | | Challenge[2] | | Necropsy Study Day |
|---|---|---|---|---|---|---|---|
| | | | Study Days | Route | Study Day | Dose | |
| T01 | Saline | 10 | 0 and 21 | SC | 42 | $10^6$ $TCID_{50}$ | 46 |
| T02 | Saline | 9 | | | | | 56 |
| T03 | CRCoV-CIV 5% AlOH | 10 | | | | | 46 |
| T04 | CRCoV-CIV 5% AlOH | 9 | | | | | 56 |
| T05 | CRCoV-CIV 5% Emulsigen ® | 9 | | | | | 46 |
| T06 | CRCoV-CIV 5% Emulsigen ® | 9 | | | | | 56 |

[1]Investigational Veterinary Product (IVP) was administered subcutaneously (SC).
[2]Target challenge dose of CRCoV Max isolate (passage 1), administered intranasally.
AlOH: Aluminum hydroxide gel A heterologous CRCoV isolate ("Max" strain; passage 1) was used as the challenge material. The virus stock material was propagated and titrated on HRT18G cells and determined to have a titer of $10^{7.1}$ $TCID_{50}$/mL. This challenge material was tested and confirmed satisfactory for sterility testing, being free of mycoplasma and canine/feline extraneous agents.

Animals were vaccinated with the appropriate vaccine or placebo on Days 0 and 21 (Table 2.). The first vaccination was administered in the right shoulder region on Day 0, and the second vaccination was administered in the left shoulder region on Day 21.

Animals were observed daily for injection swelling/pain after first vaccination from study days 0 to 8, and thereafter on study days 12, 15, 19, 21, 22, and 26. On study day 8, swelling observations for 18 animals were inadvertently not recorded. On study day 21, extra observations for right shoulder (first dose vaccination) observations were recorded for some animals.

After vaccination on study day 21, animals were observed daily for injection swelling/pain post vaccination on study days 21 to 29, and thereafter on study days 33, 36, and 40. All swellings resulting from the second vaccination were resolved by study Day 40. Tympanic temperatures were collected on Vaccination Days 0 to 7 and 21 to 28, approximately 3 hours following each vaccination.

Blood samples (approximately 6 mL) for serology were collected in SST tubes on study day 42 prior to challenge. Also prior to challenge, tympanic temperatures were collected on study days 40, 41, and 42, to establish baseline values. Two types of nasal swabs (VTM for CRCoV virus isolation; Amies for bacterial isolation) were collected from each dog prior to challenge on study day 42. Animals were observed once daily pre-challenge on study days 40, 41, and 42 for clinical signs of respiratory disease, to establish baseline values.

Each group of six dogs from all treatment groups was administered the challenge virus by aerosolization of 19 mL of challenge material in the Plexiglass chamber for approximately 30 minutes. The volume of challenge virus nebulized in the chamber was adjusted proportionally when less than six dogs were challenged at a time. Virus titration performed on CRCoV challenge samples collected after challenge administration confirmed that the amount of live challenge virus aerosolized in the chamber contained $10^{5.1}$ $TCID_{50}$ mL. Post challenge, tympanic temperatures, clinical observations, and nasal swabs (Sterile Dacron Swabs, Puritan 25-806-1 PD) for virus isolation (VTM tubes) were collected daily from dogs from study day 42 to 56. Blood samples (approximately 6 mL) for serology were collected on study day 46 and study day 56 prior to necropsy.

At necropsy, the complete lung and trachea were aseptically removed and placed on a sterile drape. The lung lobes were evaluated grossly for lung lesions (consolidation). Each lung lobe was scored for percentage of lung consolidation. Lung sets from two animals had insufficient exsanguination, and could not be evaluated and scored. The trachea was transected, the lumen evaluated for gross pathology, and any findings were recorded. After the lungs had been scored, each right caudal lung lobe was lavaged by flushing with approximately 30.0 mL of VTM (no antibiotic) for diagnostic bacteriological analysis and for virus isolation.

After the lungs were scored, tissue samples were collected from the trachea, and nasal cavity, and the whole left middle lung lobe was collected for histopathology. Tissue samples were collected from the trachea, the nasal cavity, and right cranial lung lobe for virus isolation and for bacteriology.

Blood for serology was collected on pre-determined study days.

Nasal swabs (Amies transport medium without charcoal) were collected from each dog only on study day 42 (prior to challenge) for diagnostic bacteriology. These swabs were tested for the presence of *Bordetella* spp., *Pasteurella* spp., *Staphylococcus* spp., *Mycoplasma* spp. and *Streptococcus canis*.

Results.

Fifty-nine beagle puppies were confirmed by IFA testing to be negative for antibodies (IFA titer <40) against CRCoV on study day 0 prior to vaccination. Serum samples were also tested by serum neutralization and confirmed to be negative (SN titer <20) for antibodies to CRCoV. Nasal swabs evaluated for CRCoV virus isolation confirmed that all animals were free of CRCoV virus on study day 0 prior to vaccination. CIV virus and antibody testing on study day 0 confirmed that the animals to be free of CIV virus and CIV HAI antibodies (HAI titer <8). Based on these two criteria, the animals were confirmed susceptible, and therefore suitable for evaluation of the efficacy and safety of CRCoV and CIV vaccines. Saline-vaccinated controls remained CRCoV seronegative until study day 42. All animals were confirmed CRCoV-free by virus isolation study day 42, indicating lack of extraneous CRCoV exposure in the facility. All dogs were confirmed to be free of *Bordetella bronchiseptica* on study day 42 (pre-challenge).

Dogs were vaccinated with two formulations containing inactivated CRCoV and inactivated CIV antigens, adjuvanted with either Emulsigen® or Rehydragel™ CRCoV antigen potency in the vaccine was measured by a double-antibody sandwich ELISA, employing a CRCoV-specific serum neutralizing monoclonal antibody 41.1.1. Measured against a designated reference antigen, potency was determined to be 1.14 RAU/dose. The guinea pig HAI titer of CIV was 955. (Pass criterion was an HAI titer ≥161.)

Ten out of the 19 animals that received the Emulsigen® formulation (T05 and T06) developed measurable injection swelling after the first vaccination. There was scratching reported in the majority of dogs immediately following vaccination. Pain to touch was reported in only 2 dogs. Except for one dog, the swellings in this group were all resolved by the next day. There was a slight numerical increase in injection swelling in size and frequency after the second vaccination, but they were all within what is expected as a typical reaction to an adjuvanted vaccine. There was no systemic reaction reported in any of the vaccinated dogs, as confirmed by the lack of clinical fever (<39.5° C.). These findings indicate that this vaccine formulation is safe to administer to dogs at this age group, and the safety profile is within what is expected for an adjuvanted vaccine.

The majority of dogs (T03 and T04) that received the Rehydragel™ formulation developed injection swelling after each vaccination. The swellings appeared three days after the first vaccination, with the majority of swellings resolved by study day 19. A similar reaction was seen after the second vaccination, where the majority of swellings resolved by study day 36. The injection swellings were generally small in size, and typical of Alum adjuvant reactions. There was no pain and no fever reported, confirming the lack of systemic reaction to vaccination. These findings indicate that this vaccine formulation is safe to administer to dogs at this age group, and the safety profile is within what is expected for an adjuvanted vaccine.

Serum neutralization titers were tabulated, and compared between groups (FIG. 1). Both vaccine formulations induced serum neutralizing antibody (SN) responses in all the vaccinated dogs after the first dose, indicating active immunization (FIG. 1). The geometric mean SN response (GMT for Rehydragel™=552; GMT for Emulsigen®=2030) increased after the second vaccination, indicating a booster effect of the second vaccination. Both vaccine formulations resulted in a robust anamnestic SN response after challenge (GMT for Rehydragel™=10,725 and Emulsigen®=11,584 on study day 56 for the remaining dogs in the study), indicating an effective immune memory response. It is important to note that the antibody response to CRCoV was achieved in the presence of a CIV antigen, indicating lack of interference between the antigens in the bivalent vaccine.

Fifty-six dogs remaining in the study were challenged on study day 42 by aerosolization. Post-challenge nasal virus isolation demonstrated that all saline-vaccinated dogs (100%) shed challenge virus for at least three days between days 1 and 6 post challenge, indicating the infection of dogs by CRCoV, with a 4.5 mean number of days of shedding (FIG. 2). The two vaccine formulations significantly reduced the virus shedding to 2.6 days (p<0.0001) and 3.4 days (p=0.0042) for Rehydragel™ and Emulsigen®, respectively. These findings indicate that the vaccines induced efficacy that resulted in reduction of virus infection.

Tissue virus isolation data showed that 90-100% of the dogs in the saline-vaccinated group were positive for virus in their nasal cavity, trachea, and lung tissues on study day 4 post-challenge, indicating infections of the respiratory organs (FIG. 3). By contrast, both vaccines significantly reduced the percentage of animals positive for virus isolation in the lungs (p<0.0001) and in the nasal cavity (p<0.002). While both vaccines reduced virus isolation in the trachea (virus isolated from 70% for Rehydragel™ group and from 44% for Emulsigen® group), only the Emulsigen® formulation resulted in significant reduction of virus isolation when compared to the saline controls (p=0.0089). There was no virus isolated from any animals on day 14 post-challenge, indicating that the CRCoV infection is rapid in entering and leaving the respiratory tissues, a scenario similar to canine influenza. The virus isolation data indicate that both vaccine formulations significantly reduced virus infection in dogs.

The CRCoV challenge caused only mild respiratory clinical signs under experimental conditions. Ocular and nasal discharges were reported in dogs across treatment groups. Except for one animal on study day 41 (one day prior to challenge) in the saline control group, all animals had normal temperatures prior to challenge. There were two animals in the saline control group reported with clinical fever after challenge. Both dogs had temperatures of 39.6° C. on day 2 post-challenge (study day 44). One of those dogs showed fever again (40° C.) on day 4 post-challenge. That dog received treatment for concurrent gastroenteritis. This may explain the fever response following CRCoV challenge in this dog, since this virus has not been shown previously to cause fever under experimental condition. There was no clinical fever reported in any of the vaccinated dogs.

Gross necropsy evaluation of the lungs, trachea, and nasal turbinates was performed on day 4 and 14 post-challenge. There was no remarkable gross lesion reported, except for lung consolidation in two dogs from T05, two dogs from T01, and one dog from T02. The cause of these lesions was unclear, but unlikely due to CRCoV, since the lesions were not consistent, and CRCoV has not been shown to cause lung consolidation. Examination of the diagnostic bacteriology of the tissues did not suggest the involvement of any other pathogen.

The lung, trachea, and nasal cavity tissue sections were examined and scored. Depending on the extent of changes observed, a score (0 to 4) was assigned. Previous studies conducted have shown that the ciliary damage in the tracheal epithelia on day 4 post-challenge is a characteristic pathologic effect associated with CRCoV infection. (Priestnall et al 2009) The histopathology data revealed that 70% of saline-vaccinated dogs experienced some degree of tracheal ciliated-epithelial damage on day 4 post-challenge. By contrast, both vaccines reduced the number of affected dogs to 40% for the Rehydragel™ (p=0.1184) and 0% for the Emulsigen® (p=0.0003). This indicates that the vaccines induced efficacy that protected against or reduced the tracheal mucociliary damage, an important innate defense mechanism, in infected dogs.

To assess potential involvement of other respiratory pathogens in the study, animals were tested for diagnostic bacteriology prior to challenge (nasal swabs) and after challenge (lung tissue/lavage). Results obtained demonstrated that the animals were mostly free of other respiratory pathogens, indicating that the clinical outcome measured after challenge was due specifically to CRCoV infection.

In summary, all CRCoV-CIV-vaccinated dogs (100%) developed CRCoV serum neutralizing antibody titers three weeks after the second vaccination, indicating active immunization followed by strong post-challenge anamnestic response, indicating good priming of the immune system. The two vaccine formulations significantly reduced viral shedding. Both vaccine formulations significantly reduced the percentage of animals positive for virus isolation in the lungs (p<0.0001) and in the nasal cavity (p<0.002). Both vaccines reduced virus isolation in the trachea, albeit only the Emulsigen® formulation resulted in significant reduction of virus isolation when compared to the saline controls (p 0.0089). Both of the vaccines also reduced the number of tracheal ciliated-epithelial affected dogs. Efficacy of the CRCoV antigen in these vaccines was achieved in the presence of CIV antigen, indicating lack of interference on the CRCoV by CIV fraction.

Example 3

Safety and Efficacy of *Bordetella bronchiseptica*-Containing Vaccines in Dogs

Fifty (50) dogs, divided into 5 treatment groups, were selected for the study. Animals were determined to be fit for the study based on a physical examination on Day −4, Blood samples (approximately 8 mL) for serology were collected in SST tubes from all animals on Study Days −2, 21 and 28 prior to each vaccination. The serum samples collected on Day −2 were used to confirm animals were free of B. bronchiseptica. Nasal swabs were collected prior to vaccination on Day 0, and tested for the presence of B. bronchiseptica. Tympanic temperatures were collected starting on Day −4, to establish a baseline prior to vaccination.

Animals were vaccinated with the appropriate vaccine on Days 0, 21, and 28 according to the study design shown in Table 4. The vaccines were administered subcutaneously to each dog in the right shoulder region for the first vaccination, and in the left shoulder region for the second vaccination.

TABLE 4

Study Design

| Group | IVP | N | Vol (mL) | Vaccination[1] Study Days | Route | Challenge[2] Study Day | Target Dose/Dog | Route |
|---|---|---|---|---|---|---|---|---|
| T01 | B. bronschiseptica (inactivated) + Pertactin (10 µg) No Adjuvant | 10 | 1.0 | 0 and 28 | SC | 56 | $10^9$ | Intranasal (aerosol; chamber) |
| T02 | Saline | 10 | 1.0 | 0 and 28 | | | | |
| T03 | B. bronschiseptica (inactivated) + Pertactin (10 µg) No Adjuvant | 10 | 1.0 | 0 and 21 | | | | |
| T04 | CRCoV/CIV/CPIV/ CAV2 rehydrated with B. bronschiseptica (inactivated) + Pertactin (10 µg) No Adjuvant | 10 | 1.0 | 0 and 28 | | | | |
| T05 | CRCoV/CIV/CPIV/ CAV2 rehydrated with water (diluent) | 10 | 1.0 | 0 and 28 | | | | |

[1]Investigational Veterinary Product (IVP) was administered (SC) subcutaneously.
[2]Target challenge dose of $10^9$ organisms of Bordetella bronchiseptica strain.

All animals were observed on vaccination Days 0, 21, and 28 for injection site reactions following vaccination. They were observed daily for injection reactions post vaccination from Days 1 to 7 and 22-35. Tympanic temperatures were collected on Days 0 to 7 and 21 to 35.

Blood samples (approximately 6 mL) for serology were collected on Day 55, one day prior to challenge. Tympanic temperatures were collected on Days 54, 55, and 56 prior to challenge. Nasal swabs were collected on Day 55, one day prior to challenge, and tested for the presence of B. bronchiseptica. Animals were observed twice daily (a.m. and p.m.), approximately 30 minutes each session on Days 54 and 55, and in the a.m. on Day 56, for clinical signs of respiratory disease, in order to establish baseline values.

Bordetella bronchiseptica challenge strain was used to prepare a target challenge dose of $10^9$ CFU/4 mL/dog. On Day 56, dogs from all treatment groups were challenged intranasally with B. bronchiseptica by aerosolization in a Plexiglas chamber for a total of 30 minutes for each pen challenged. Five dogs from the same pen (one from each treatment group) were challenged at a time.

Tympanic temperatures was recorded once daily after challenge from Days 56 to 77. Clinical observations were performed twice daily (a.m. and p.m.), for approximately 30 minutes in each room per each session, from Day 56 and until Day 76 and once (a.m.) on Day 77. Briefly, cough, nasal discharge, sneeze, ocular discharge, retch, and depression were observed using the following scoring system: Absent (O), Mild (1), Moderate (2), and Severe (3). Nasal swabs were collected on Days 59, 62, 66, 69, 74, 76 and 77, to determine shedding of challenge organisms.

Blood samples (approximately 6 mL) for serology were collected on Day 77. Nasal swabs for isolation of B. bronchiseptica were collected using swabs and transport media.

Agglutinating antibodies to B. bronchiseptica were determined by the Micro Agglutination Test (MAT). Serum samples from treatment groups T04 and T05 from Days 0, 28, 55, and 77 were titrated for CRCoV antibodies by serum neutralization and IFA, and for CIV by HAI. B. bronchiseptica isolation from nasal swabs was performed according to standard procedure. Each sample was tested qualitatively for the presence or absence of bacteria.

Results.

Fifty (50) healthy approximately 8-week-old beagle puppies were confirmed by nasal swab culture isolation to be free of B. bronchiseptica organisms on Day 0. Serum samples evaluated for B. bronchiseptica agglutinating antibodies by the MAT confirmed that all puppies were susceptible with MAT titers of 8 on Day −2.

All experimental vaccines evaluated in this study produced mild to no injection swellings after the first vaccination. Injection swellings were limited to study day 0 for the majority of vaccinates. Mild to no injection swellings were also reported after the second vaccination. The injection site swellings when they occurred, resolved between one to three days after the second vaccination. Scratching was reported predominantly in the 5-way combination group (T04). There was no clinical fever reported after vaccinations. There were no injection swellings reported in the saline group. The data confirmed the safety of the vaccines.

The colony count performed before and after challenge inoculation confirmed that an average of $1.45 \times 10^8$ CFU Bordetella per dog were aerosolized in the chamber. Challenge inoculation induced cough in all saline control dogs (T02) with a mean percentage observation coughed of 43.5% and 12.2 days coughed. Treatment group T05, vaccinated with 4-way viral only (CRCoV/CIV/CPIV/CAV2) without Bordetella antigen developed cough similar to the saline control with a mean percentage observation coughed of 43.4% and 12.2 days coughed. These findings indicate that the challenge was adequate and consistent to evaluate the test vaccines.

Dogs in treatment group T01 vaccinated with the Bordetella vaccine were significantly protected against challenge (3.6 days coughed, $p<0.0001$) when compared to the control group (12.2 days coughed). The same vaccine also significantly protected dogs in T03 when given at 3-weeks interval regimen (5.8 days coughed, $p=0.0004$). The reduction in cough scores in these two groups (T01 vs T03) was not significantly different (p-value=0.1883) suggesting that the level of protection for the vaccine given with a 3 or 4 weeks interval, is similar.

Dogs in T04 that received the non-adjuvanted 5-way combination vaccine were significantly ($p=0.0016$) protected against Bordetella challenge (6.6 days coughed) when compared to the saline controls (12.2 days coughed), and when compared to T05 receiving the 4-way viral (CRCoV/CIV/CPIV/CAV2) combination (12.1 days coughed, $p=0.0019$) indicating efficacy of the Bordetella fraction in the combination vaccine lacking adjuvant.

Serological evaluation of the viral fractions in the 5-way combination vaccine was possible for only two fractions, the CIV and CRCoV, where dogs were confirmed seronegative on study day −2. CIV HAI response in the 4-way vaccine group (T04) on study day 56 were numerically similar to that in the 5-way vaccine group (T05) and indicate lack of interference by the Bordetella fraction on the CIV antigen. CRCoV SN responses on study day 56 were numerically higher in the 4-way vaccine group (T04) than in the 5-way vaccine group (T05), indicating possible interference by the Bordetella on the CRCoV fraction. However, these findings are not conclusive since these vaccines were not adjuvanted and the formulation was not optimized and CRCoV challenge was not conducted to test efficacy.

The monovalent Bordetella vaccine was confirmed to be safe and efficacious. The efficacy of the monovalent vaccine was demonstrated when the vaccine was given at 21- or 28-day intervals. The Bordetella fraction was also shown to be efficacious when given in a 5-way non-adjuvanted combination vaccine.

Example 4

Multivalent Serology Study

Forty dogs, approximately 8 weeks of age and in good general health, were pre-screened for Bordetella bronchiseptica by Micro Agglutination Test (MAT), and for canine respiratory coronavirus (CRCoV) by indirect fluorescent antibody assay (IFA). Serum neutralization (SN) was also used to evaluate antibody levels. On Day 0, all dogs were negative for antibodies to Bordetella bronchiseptica as determined by MAT ($\leq 16$), and negative for antibodies to CRCoV as determined by IFA ($<40$). All dogs were also free of Bordetella bronchiseptica and CRCoV, as determined by nasal swab isolation test prior to first vaccination (Day 0).

Dogs were divided into 5 treatment groups of 8 dogs each, and vaccinated according to the study design shown in Table 1. The vaccines were administered to each dog in the right shoulder region for the first vaccination, and in the left shoulder region for the second vaccination.

TABLE 2

Study Design

| Treatment Group | Investigational Veterinary Product (IVP) | Adjuvant | N | Vaccination[1] Study Days | Route |
|---|---|---|---|---|---|
| T01 | CAV2/CPIV/CPV/L4 | 5% Rehydragel | 8 | 0 and 21 | Subcutaneously (SC) |
| T02 | CAV-2, CPI, CRCoV+ Bordetella, CIV | QCDC | 8 | | |
| T03 | CAV-2, CPI, CRCoV+ Bordetella, CIV | 1% EMA[1]/ 3% Neocryl/ 5% Emulsigen SA | 8 | | |
| T04 | CAV-2, CPI, CRCoV+ Bordetella, CIV | QCDC | 8 | | |
| T05 | CAV-2, CPI, CRCoV+ Bordetella, CIV | QCDC | 8 | | |

[1]EMA = ethylene maleic anhydride

Following the second vaccination, due to complications, groups T04 and T05 were removed from the study. Dogs in the remaining groups (T01, T02, and T03) were observed daily for post vaccination reactions, and monitored for body (tympanic) temperature for 7 days after each vaccination. Blood samples were collected from dogs on Days 0, 21, 42 and 56 to measure antibody responses.

Serum samples from Day 0, 21, 42 and 56 were tested for agglutinating antibodies to Bordetella bronchiseptica by the MAT assay. Serum samples from the same days were also titrated for CRCoV antibodies by serum neutralization, for CIV by HAI, and for CAV-2 and CPI antibodies by serum neutralization. Geometric mean antibody titers were obtained for each treatment group.

The test vaccines in groups T02 and T03 induced antibody responses in all (100%) the vaccinated dogs after the second dose, indicating active immunization against the viral antigens. The antibody response increased after the second vaccination in the majority of vaccinated dogs, indicating a booster effect of the second vaccination. It is important to note that the antibody responses among the viral fractions was achieved in the presence of multiple viral and bacterial (B. bronchiseptica) antigens, indicating lack of immunological interference. The MAT serology is not correlative to protection against Bordetella, but is rather a valuable screening tool to enroll suitable study animals. In conclusion, based on the immunological response in vaccinated dogs, efficacy of the viral antigens is predicted in the 5 way multivalent vaccine.

Example 5

Duration of Immunity Study

The purpose of this study is to demonstrate the duration of immunity of a multivalent respiratory combination vaccine in dogs. The vaccine contains the following antigenic components: modified-live CAV-2, modified-live CPIV, inactivated CIV, inactivated CRCoV and a *Bordetella bronchiseptica* extract supplemented with a recombinant antigen, either pertactin, Bsp22, or both.

All animals are in good general health, and have not received any vaccinations for any of the pathogens for which the vaccine is designed to protect against. Dogs are divided into multiple sets of treatment groups. Each set consists of two treatment groups, a control group receiving a placebo vaccine, and a vaccinate group receiving the test vaccine. Animals are vaccinated twice, approximately 2-4 weeks apart. They are observed for injection site reactions following each vaccination.

Approximately 3-12 months following vaccination, each set of two treatment groups (vaccinates and controls) are challenged with one of the pathogens for which the vaccine is designed to protect against. Clinical observations are performed leading up to and following challenge. Nasal swabs for isolation of the challenge pathogen are collected during the post challenge period. Blood from each animal is collected for obtaining serum, which is used for subsequent analytical analysis. Clinical signs of respiratory disease, pathogen shedding post challenge, and serological responses are used as criteria to judge the efficacy of vaccines.

All of the foregoing references are hereby incorporated by reference as if set forth fully herein.

Having thus described in detail various embodiments of the present invention, it is to be understood that the invention defined by the appended claims is not to be limited to particular details set forth in the above description as many apparent variations thereof are possible without departing from the spirit or scope of the present invention.

We claim:

1. A vaccine composition comprising a canine influenza virus (CIV), canine respiratory coronavirus (CRCoV), and an adjuvant selected from the group consisting of an aluminum hydroxide gel, an oil-in-water emulsion, a water-in-oil emulsion, and a triterpenoid-containing preparation, wherein said CIV is deposited with the ATCC as PTA-7694, and said CRCoV is deposited with the ATCC as PTA-11444.

2. The vaccine composition ref claim 1, further comprising *Bordetella bronchiseptica*.

3. The vaccine composition of claim 2, further comprising a p68 pertactin antigen.

4. The vaccine composition of claim 2, wherein said *Bordetella bronchiseptica* is a bacterin or a bacterial extract.

5. The vaccine composition of claim 2, further comprising a canine parainfluenza virus (CPIV) antigen or canine adenovirus type 2 (CAV-2) antigen.

6. The vaccine composition of claim 5, wherein the CPIV antigen is CPIV and the CAV-2 antigen is CAV-2.

7. The vaccine composition of claim 2, wherein said composition is non-adjuvanted.

8. The vaccine composition of claim 1, wherein said composition does not contain a non-respiratory antigen.

9. The vaccine composition of claim 1, wherein said composition treats or prevents canine infectious respiratory disease complex (CIRDC) in a canine.

10. A method of treating or preventing CIRDC in a canine comprising administering to said canine the immunogenic composition of claim 1.

11. The method of claim 10, wherein said composition prevents CIRDC for a period of about six months or more.

12. The method of claim 10, wherein said composition prevents CIRDC for a period of about one year.

13. The vaccine composition of claim 1, wherein administration of said composition to a canine protects said canine against CRCoV infection.

* * * * *